(12) United States Patent
Yang et al.

(10) Patent No.: US 11,041,007 B2
(45) Date of Patent: *Jun. 22, 2021

(54) MODIFIED INTERLEUKIN-7 PROTEIN

(71) Applicant: GENEXINE, INC., Seongnam-si (KR)

(72) Inventors: Se Hwan Yang, Seoul (KR); Donghoon Choi, Yongin-si (KR); Hye Seong Lim, Seongnam-si (KR)

(73) Assignee: GENEXINE, INC., Seongnam-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/219,183

(22) Filed: Dec. 13, 2018

(65) Prior Publication Data

US 2019/0106471 A1    Apr. 11, 2019

Related U.S. Application Data

(63) Continuation of application No. 15/126,313, filed as application No. PCT/KR2016/006214 on Jun. 10, 2016, now Pat. No. 10,208,099.

(30) Foreign Application Priority Data

Jun. 11, 2015   (KR) ........................ 10-2015-0082793

(51) Int. Cl.
*C07K 14/54* (2006.01)
*A61K 38/00* (2006.01)

(52) U.S. Cl.
CPC .......... *C07K 14/5418* (2013.01); *A61K 38/00* (2013.01); *C07K 2319/00* (2013.01); *C07K 2319/02* (2013.01); *C07K 2319/30* (2013.01)

(58) Field of Classification Search
CPC ................................................ C07K 14/5418
See application file for complete search history.

(56) References Cited

U.S. PATENT DOCUMENTS

| | | | |
|---|---|---|---|
| 5,093,242 A | 3/1992 | Bachmair et al. | |
| 6,153,380 A | 11/2000 | Nolan et al. | |
| 7,585,947 B2 | 9/2009 | Morre et al. | |
| 7,589,179 B2 | 9/2009 | Gillies et al. | |
| 8,153,114 B2 | 4/2012 | Morre et al. | |
| 10,208,099 B2 * | 2/2019 | Yang ...................... | A61P 31/14 |
| 2002/0127564 A1 | 9/2002 | Nolan | |
| 2005/0164352 A1 | 7/2005 | Lauder et al. | |
| 2005/0249701 A1 | 11/2005 | Morre et al. | |
| 2008/0206190 A1 | 8/2008 | Morre et al. | |
| 2008/0300188 A1 | 12/2008 | Yang et al. | |
| 2010/0196312 A1 | 8/2010 | Morre et al. | |
| 2011/0243887 A1 | 10/2011 | Lauder et al. | |
| 2012/0016104 A1 | 1/2012 | Morre et al. | |
| 2013/0217864 A1 | 8/2013 | Cho et al. | |
| 2014/0178393 A1 | 6/2014 | Andres et al. | |
| 2014/0377218 A1 | 12/2014 | Morre et al. | |

FOREIGN PATENT DOCUMENTS

| | | |
|---|---|---|
| EP | 0 314 415 B1 | 8/1994 |
| EP | 0 877 752 B1 | 5/2003 |
| JP | 2-501618 A | 6/1990 |
| JP | 2501618 B2 | 3/1996 |
| JP | 2000-504220 A | 4/2000 |
| JP | 2001-509661 A | 7/2001 |
| JP | 2009-501543 A | 1/2009 |
| JP | 2010-531134 A | 9/2010 |
| JP | 2014-147396 A | 8/2014 |
| JP | 2015-57392 A | 3/2015 |
| KR | 10-2006-0112673 A | 11/2006 |
| KR | 10-2009-0045953 A | 5/2009 |
| KR | 10-2012-0041139 A | 4/2012 |
| KR | 10-2014-0004802 A1 | 1/2014 |
| KR | 10-2017-0066265 A | 6/2017 |
| WO | 2005/021592 A2 | 3/2005 |
| WO | 2007/019232 A2 | 2/2007 |
| WO | 2009/101737 A1 | 8/2009 |
| WO | 2015/015516 A2 | 2/2015 |

OTHER PUBLICATIONS

European Patent Office; Search Report dated Dec. 19, 2018 issued in counterpart application No. 16807859.0.
Japanese Patent Office; Office Action dated Jan. 8, 2019 issued in counterpart application No. 2017-564121.
International Search Report of PCT/KR2016/012495 dated Jan. 13, 2017.
NCBI, Pdb: 4C54_A (Feb. 5, 2014), "Chain A, Crystal Structure of Recombinant Human IgG4 Fc" (3 pages total).
Bowie et al., "Deciphering the Message in Protein Sequences: Tolerance to Amino Acid Substitutions", Science, vol. 247, pp. 1306-1310, 1990 (5 pages total).
Bork, "Powers and Pitfalls in Sequence Analysis: The 70% Hurdle", Genome Research, vol. 10, pp. 398-400, 2000 (4 pages total).
Lazar et al., "Transforming Growth Factor alpha: Mutation of Aspartic Acid 47 and Leucine 48 Results in Different Biological Activities", Molecular and Cellular Biology, vol. 8, No. 3, pp. 1247-1252, 1988 (6 pages total).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", The Journal of Cell Biology, vol. 111, pp. 2129-2138, 1990 (10 pages total).
International Search Report for PCT/KR2016/013966 dated Mar. 2, 2017 [PCT/ISA/210].
Moon Cheol Kang, et al., "Intranasal Introduction of Fc-Fused Interleukin-7 Provides Long-Lasting Prophylaxis against Lethal Influenza Virus Infection", Journal of Virology, Mar. 2016, pp. 2273-2284, vol. 90, No. 5.
Nam, et al., "Marked enhancement of antigen-specific T-cell responses by IL-7-fused nonlytic, but not lytic, Fc as a genetic adjuvant", Eur. J. Immunol., 2010, vol. 40, pp. 351-358 (8 pages total).

(Continued)

*Primary Examiner* — Prema M Mertz
(74) *Attorney, Agent, or Firm* — Sughrue Mion, PLLC

(57) ABSTRACT

The present invention provides a modified interleukin-7 and a use thereof. The modified IL-7 or an IL-7 fusion protein of the present invention comprising the same can be obtained in high yield, and biologically active in viral infection and cancer models. Therefore, they can be used for the prevention and treatment of various diseases.

12 Claims, 11 Drawing Sheets
(1 of 11 Drawing Sheet(s) Filed in Color)
Specification includes a Sequence Listing.

(56) References Cited

OTHER PUBLICATIONS

Yong Bok Seo, et al., "Crucial Roles of Interleukin-7 in the Development of T Follicular Helper Cells and in the Induction of Humoral Immunity", Journal of Virology, Aug. 2014, pp. 8998-9009, vol. 88, No. 16.
Fry et al.; "Interleukin-7: from bench to clinic"; Blood, Jun. 1, 2002 vol. 99, No. 11; pp. 3892-3904.
GenBank, "interleukin-7 [synthetic construct]", Accession No. AAB70834.1 (Sep. 21, 1997), total 1 page.
Heufler et al.; "Interleukin 7 Is Produced by Murine and Humane Keratinocytes"; J. Exp. Med.; The Rockefeller University Press; vol. 178; Sep. 1993; pp. 1109-1114.
International Preliminary Report on Patentability and Written Opinion of the International Searching Authority issued Dec. 12, 2017 for International Application No. PCT/KR2016/006214.
International Search Report for related International Application No. PCT/KR2016/006214.
Kroncke et al.; "Human follicular dendritic cells and vascular cells produce interleukin-7: a potential role for interleukin-7 in the germinal center reaction"; Eur. J. Immunol. 1996. 26: 2541-2544.
Marc Pellegrini et al.; "IL-7 Engages Multiple Mechanisms to Overcome Chronic Viral Infection and Limit Organ Pathology"; Cell 144, 601-613, Feb. 18, 2011.
Muegge et al.; "Interleukin-7: A Cofactor for V(D)J Rearrangement of the T Cell Receptor β Gene"; Science; Vol. 261; Jul. 2, 1993; pp. 93-95.
Nanjappa et al.; "Immunotherapeutic effects of IL-7 during a chronic viral infection in mice"; Blood, May 12, 2011 vol. 117, No. 19; pp. 5123-5132.
Patel et al.; "Treatment of progressive multifocal leukoencephalopathy and idiopathic CD41 lymphocytopenia"; J Antimicrob Chemother 2010; 65: 2489-2492; publication Oct. 20, 2010.
Pellegrini et al.; "Adjuvant IL-7 antagonizes multiple cellular and molecular inhibitory networks to enhance immunotherapies"; nature medicine; vol. 15; No. 5; May 2009; pp. 528-536, 819.
Rosenberg et al.; "IL-7 Administration to Humans Leads to Expansion of CD8+ and CD4+ Cells but a Relative Decrease of CD4+ T-Regulatory Cells"; National Institute of Health; Nih Public Access Author Manuscript; J Immunother: 2006; 39(3): 313-319.
Sawa et al.; "Hepatic Interleukin-7 Expression Regulates T Cell Responses"; Immunity 30, 447-457, Mar. 20, 2009.
Snyder et al.; "IL-7 in allogeneic transplant: Clinical promise and potential pitfalls"; Leukemia & Lymphoma, Jul. 2006; 47(7): 1222-1228.
Watanabe et al.; "Interleukin 7 Is Produced by Human Intestinal Epithelial Cells and Regulates the Proliferation of Intestinal Mucosal Lymphocytes"; J. Clin. Invest. vol. 95, Jun. 1995, pp. 2945-2953.
Mikayama et al. Proc. Natl. Acad. Sci. USA (1993) vol. 90, pp. 10056-10060.
Voet et al. Biochemistry John Wiley & Sons, Inc., (1990) pp. 126-128 and 228-234.
European Patent Office; Communication dated May 15, 2019 in counterpart application No. 16807859.0.
International Search Report of PCT/KR2016/014127 dated Mar. 9, 2017.
Whisstock et al., "Prediction of protein function from protein sequence and structure", Quarterly Reviews in Biophysics, 2003, vol. 36, No. 3, pp. 307-340.
Maryam Fazeli et al., "Efficacy of HPV-16 E7 Based Vaccine in a TC-1 Tumoric Animal Model of Cervical Cancer", Cell Journal, vol. 12. No. 4 , 2011, pp. 483-488 (6 pages total).

* cited by examiner

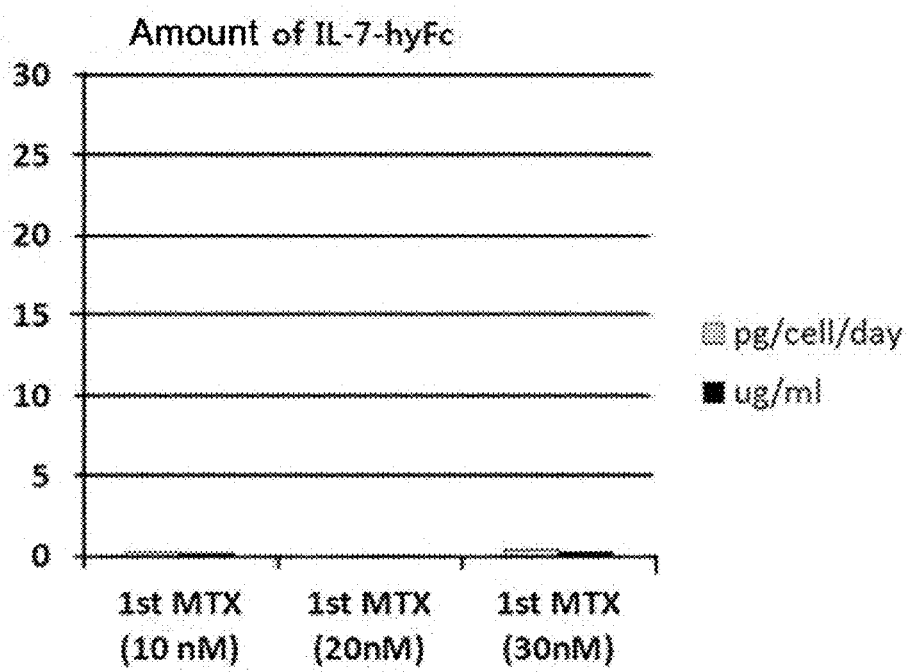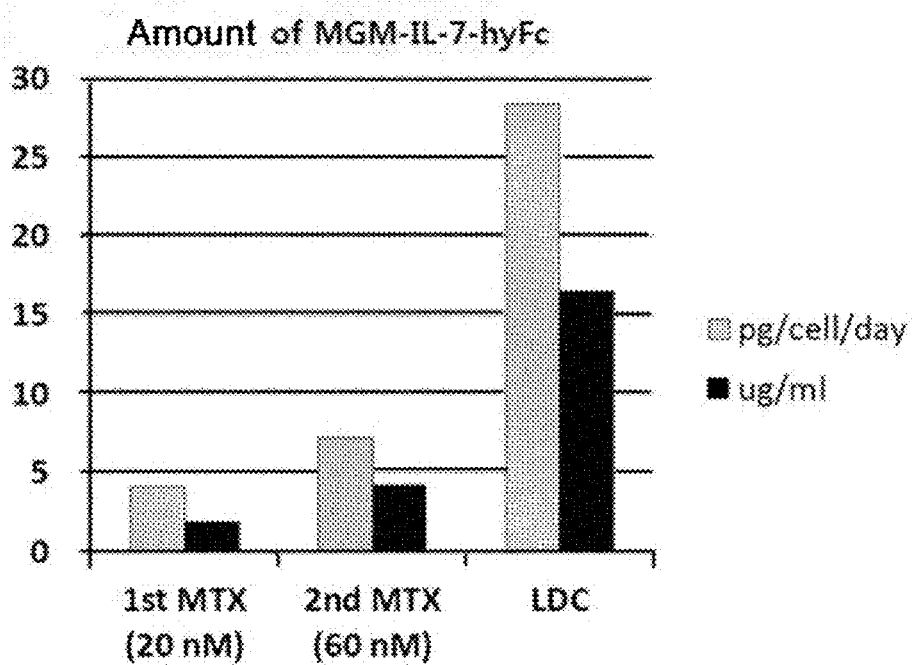

MODIFIED INTERLEUKIN-7 PROTEIN

CROSS REFERENCE TO RELATED APPLICATIONS

This application is a Rule 53(b) Continuation Application of U.S. application Ser. No. 15/126,313 filed Sep. 15, 2016, which is a National Stage of International Application No. PCT/KR2016/006214 filed Jun. 10, 2016, claiming priority based on Korean Patent Application No. 10-2015-0082793 filed Jun. 11, 2015, the contents of all of which are incorporated herein by reference in their entirety.

FIELD OF THE PRESENT INVENTION

The present invention relates to modified interleukin-7 protein and uses thereof.

BACKGROUND OF THE PRESENT INVENTION

Interleukin-7 or a polypeptide having a similar activity thereto (hereinafter, 'IL-7') is an immunostimulatory cytokine which can promote immune responses mediated by B cells and T cells, and in particular, IL-7 plays an important role in an adaptive immune system. IL-7 is mostly secreted by stromal cells in the bone marrow and thymus, but it is also produced by keratinocytes, dendritic cells, hepatocytes, neurons, and epithelial cells (Heufler C et al., 1993, J. Exp. Med. 178 (3): 1109-14; Kroncke R et al., 1996, Eur. J. Immunol. 26 (10): 2541-4: Sawa Y et al., 2009, Immunity 30 (3): 447-57; Watanabe M et al., 1995, J. Clin. Invest. 95 (6): 2945-53).

Specifically, IL-7 activates immune functions through the survival and differentiation of T cells and B cells, survival of lymphoid cells, stimulation of activity of natural killer (NK) cell, etc., and in particular, IL-7 is important for the development of T cells and B cells. IL-7 binds to hepatocyte growth factor (HGF) and functions as a pre-pro-B cell growth-stimulating factor and a cofactor for V(D)J rearrangement of the T cell receptor beta (TCRβ) (Muegge K, 1993, Science 261 (5117): 93-5).

Additionally, IL-7 regulates the development of lymph nodes through lymphoid tissue inducer (LTi) cells and promotes the survival and division of naive T cells or memory T cells. According to the clinical results on viral infection reported recently, IL-7 maintains naive T cells or memory T cells (Amila Patel, J Antimicrob Chemother 2010). Furthermore, IL-7 enhances immune response in human by promoting the secretion of IL-2 and interferon-γ.

That is, IL-7 is a cytokine for promoting the survival and proliferation of T cells, B cells, and other immune cells, and it is an excellent candidate material for an immune therapeutic agent which is applicable in various diseases, such as viral infection, cancer, and immune system injury. Recently, several clinical studies on malignancies and human immunodeficiency virus (HIV) infection confirmed the effect of IL-7 on increasing the immunity in human bodies (Fry T J et al., 2002, Blood 99 (11): 3892-904; Muegge K et al., 1993, Science 261 (5117): 93-5; Rosenberg S A et al., J. Immunother. 29 (3): 313-9). Additionally, IL-7 is also used for the immune recovery after the transplantation of allogenic stem cells (Snyder K M, 2006, Leuk. Lymphoma 47 (7): 1222-8) and the treatment of lymphopenia.

Cancer is life threatening disease. Cancer cells provide an environment that can inhibit immune system so that they can grow without being recognized by immune cells. Cancer patients show an immune deterioration in which T cells are reduced mainly due to anticancer treatment (e.g. chemotherapy, radio-therapy) or showed reduced number at the time of cancer diagnosed. Additionally, although cytotoxic T lymphocytes, effector T cells, and macrophages are gathered inside the cancer tissue, they cannot effectively remove cancer cells. Further, immune cells cannot effectively inhibit the proliferation of cancer cells because T regulatory cells (Treg), myeloid-derived suppression cells (MDSC), etc., which inhibit the function of immune effector cells, are present in cancer tissue.

Under these circumstances, immune therapies are highlighted recently. Immune therapy can be used in combination with chemotherapy or radiation therapy which are currently used for cancer treatment. In particular, the utilization of IL-7 is considered as an alternative for enhancing immune functions by overcoming the lymphopenia in which the number of T cells decrease.

Chronic infection is sustained by inducing exhaustion of T cells that recognize viruses. For example, by being infected with viruses such as HIV, hepatitis B (HBV), hepatitis C (HCV) and simian immunodeficiency virus (SIV), initial immune response is strongly induced, but the functions of virus-specific T cells gradually decrease along with time. In particular, the functions of the virus-specific T cells are reduced by PD-1, LAG-3, TIM-3, IL-10 receptor, TGF-β receptor, etc.

However, IL-7 recovers the loss of functions of the virus-specific T cells or inhibits the decrease of their functions by overcoming the immune inhibitory signal system (Pellegrini M, 2009 May; 15 (5): 528-36). Further, IL-7 induces the proliferation of T cells and increases the expression of Bcl-2 thereby promoting the expansion and survival of T cells.

Additionally, IL-7 produces cytokines and helps to retain their functions by inhibiting the expression of SOCS3, which is a mediator for inhibiting cytokine signaling. Further, IL-7 reduces immunopathology due to the production of IL-22 (Som G. Nanjappa, Blood. 2011; 117 (19): 5123-5132, Marc Pellegrini, Cell 144, 601-613, Feb. 18, 2011).

However, when a recombinant IL-7 is produced for the purpose of medicinal utilization, there are problems in that impurities increase compared to the general recombinant proteins, the amount of IL-7 degradation, and large-scale production cannot be easily achieved. Previously, Cytheris Inc. has been developed a synthetic IL-7, which is a conformer having particular disulfide-bonds (Cys: 1-4; 2-5; 3-6) (U.S. Pat. No. 7,585,947). However, since production of synthetic IL-7 requires a complicated denaturation process, the manufacturing process is not easy. Accordingly, there are strong needs for developing a modified IL-7 protein which can be produced in large-scale and by an easy manufacturing process.

In this regard, the modified IL-7, which can be produced in large-scale and by an easy manufacturing process, was manufactured, thereby completing the present invention.

SUMMARY OF THE PRESENT INVENTION

It is an object of the present invention is to provide a modified IL-7.

It is another object of the present invention is to provide a fusion proteins including a modified IL-7.

It is a further object of the present invention is to provide a nucleic acid encoding the modified IL-7 or a fusion proteins including the same, a vector including the nucleic acid and a host cell including the vector, and a method for preparing a modified IL-7 or a fusion proteins including the same.

It is a still further object of the present invention is to provide a pharmaceutical composition comprising the modified IL-7 or a fusion proteins including the same, and uses thereof.

In order to achieve the above objects, the present invention provides a modified IL-7, to which an oligopeptide consisting of 1 to 10 amino acids is linked.

Additionally, the present invention provides an IL-7 fusion proteins, comprising a first domain comprising a polypeptide having the activity of IL-7 or a similar activity thereof; a second domain comprising an amino acid sequence having 1 to 10 amino acid residues consisting of methionine, glycine, or a combination thereof; and a third domain which prolongs the half-life of the interleukin-7 fusion proteins.

Additionally, the present invention provides a nucleic acid encoding the modified IL-7 or an IL-7 fusion proteins, an expression vector comprising the nucleic acid, and a host cell comprising the expression vector.

Additionally, the present invention provides a method of producing or preparing a modified IL-7 or an IL-7 fusion proteins using the nucleic acid, the expression vector, and the host cell.

Additionally, the present invention provides a method of preventing or treating a disease using the modified IL-7 or an IL-7 fusion proteins.

The modified IL-7 of the present invention is produced without a denaturation process in high yield. Accordingly, the modified IL-7 of the present invention or a fusion proteins including the same can be applicable in various medicinal fields.

BRIEF DESCRIPTION OF THE DRAWING

The patent or application file contains at least one drawing executed in color. Copies of this patent or patent application publication with color drawing(s) will be provided by the Office upon request and payment of the necessary fee.

The above and other objects and features of the present invention will become apparent from the following descriptions of the present invention, when taken in conjunction with the accompanying drawings.

FIGS. 2(A) and 2(B) show the results of the evaluation of daily one cell unit productivity (pg/cell/day, p/c/d) of the IL-7 fusion protein prepared, in which FIG. 2(A) shows the amount of IL-7-hyFc in culture media and FIG. 2(B) shows the amount of culturing MGM-IL-7-hyFc in culture media.

DETAILED DESCRIPTION OF THE PRESENT INVENTION

Figure 1A:
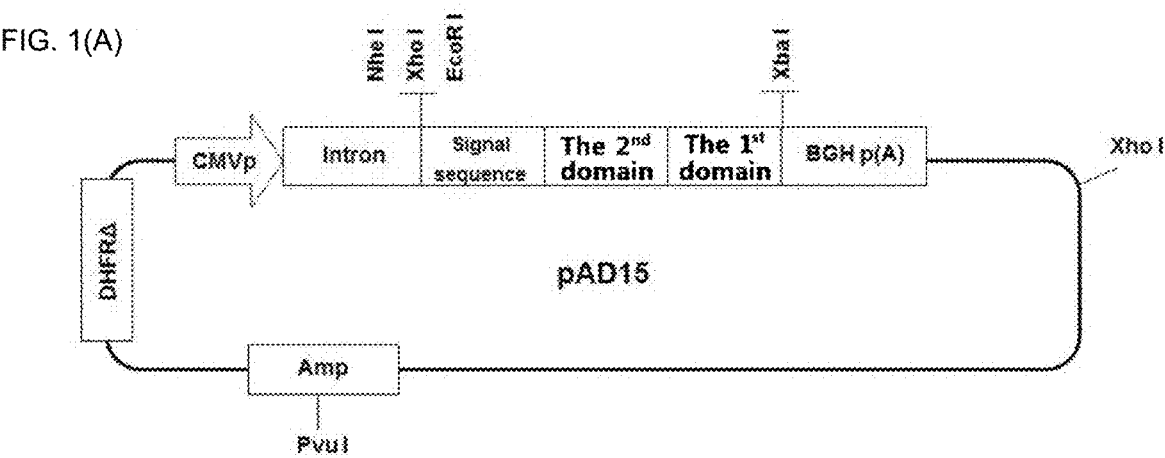
FIGS. 1(A) and 1(B) are schematic diagrams of a gene construct for producing a modified IL-7 of the present invention or a fusion proteins including the same.

The present invention provides a modified IL-7 having the following structure:

A-IL-7;

wherein A is an oligopeptide consisting of 1 to 10 amino acid residues, and IL-7 is an interleukin 7 or a polypeptide having a similar activity thereto.

As used herein, the term "a polypeptide having the activity of IL-7 or a similar activity thereof" refers to a polypeptide or protein having the same or similar sequence and activity to IL-7. Unless otherwise specified in the present invention, the term can be used as a concept which is interchangeable with the first domain of the IL-7 fusion proteins.

The IL-7 includes a polypeptide consisting of an amino acid sequence represented by SEQ ID NOS: 1 to 6. Additionally, IL-7 may have a sequence identity of about 70%, 75%, 80%, 85%, 90%, 91%, 92%, 93%, 94%, 95%, 96%, 97%, 98%, or 99% or higher, to the sequences of SEQ ID NOS: 1 to 6.

The IL-7 may include an IL-7 protein or a fragment thereof. In particular, IL-7 may be one derived from humans, rats, mice, monkeys, cows, or sheep.

Specifically, human IL-7 may have an amino acid sequence represented by SEQ ID NO: 1 (Genbank Accession No. P13232); rat IL-7 may have an amino acid sequence represented by SEQ ID NO: 2 (Genbank Accession No. P56478); mouse IL-7 may have an amino acid sequence represented by SEQ ID NO: 3 (Genbank Accession No. P10168); monkey IL-7 may have an amino acid sequence represented by SEQ ID NO: 4 (Genbank Accession No. NP_001279008); cow IL-7 may have an amino acid sequence represented by SEQ ID NO: 5 (Genbank Accession No. P26895), and sheep IL-7 may have an amino acid sequence represented by SEQ ID NO: 6 (Genbank Accession No. Q28540).

Additionally, the IL-7 protein or a fragment thereof may include variously modified proteins or peptides, i.e., variants. The above modification may be performed by a method of a substitution, a deletion, or an addition of at least one protein to the wild type IL-7, without modifying the function of the IL-7. These various proteins or peptides may have a homology of 70%, 75%, 80%, 85%, 90%, 91%, 92%, 93%, 94%, 95%, 96%, 97%, 98%, or 99%, to the wild type protein.

Conventionally, a wild type amino acid residue is substituted with alanine, but the substitution may be performed a conservative amino acid substitution, which does not affect or gives a weak effect on the entire protein charge, i.e., polarity or hydrophobicity.

For the conservative amino acid substitution, Table 1 below may be referred to.

TABLE 1

| | |
|---|---|
| Basic | Arginine (Arg, R) |
| | Lysine (Lys, K) |
| | Histidine (His, H) |
| Acidic | Glutamic acid (Glu, E) |
| | Aspartic acid (Asp, D) |
| Uncharged polar | Glutamine (Gln, O) |
| | Asparagine (Asn, N) |
| | Serine (Ser, S) |
| | Threonine (Thr, T) |
| | Tyrosine (Tyr, Y) |
| Non-polar | Phenylalanine (Phe, F) |
| | Tryptophan (Trp, W) |
| | Cystein (Cys, C) |
| | Glycine (Gly, G) |
| | Alanine (Ala, A) |
| | Valine (Val, V) |
| | Proline (Pro, P) |
| | Methionine (Met, M) |
| | Leucine (Leu, L) |
| | Norleucine |
| | Isoleucine |

For each amino acid, additional conservative substitution includes "a homolog" of the amino acid. In particular, the "homolog" refers to an amino acid, in which a methylene group (CH2) is inserted to the side chain of the beta position of the side chain of the amino acid. Examples of the "homolog" may include homophenylalanine, homoarginine, homoserine, etc., but is not limited thereto.

As used herein, the term "IL-7 protein" may be used as a concept to include "IL-7 protein and a fragment thereof" Unless otherwise specified, the terms "protein", "polypeptide", and "peptide" may be used as an interchangeable concept.

In the structure of the modified IL-7, A may be directly linked to the N-terminal of IL-7, or linked through a linker, and unless otherwise specified, the term may be used as a concept which can be interchangeable with the second domain of IL-7 fusion proteins.

In the present invention, A may be linked to the N-terminal of IL-7. The A is characterized in that it includes 1 to 10 amino acids, and the amino acid may be selected from the group consisting of methionine, glycine, and a combination thereof.

Methionine and glycine do not induce immune responses in the human body. The protein therapeutics produced from E. coli always include methionine in the N-terminal but no adverse reactions have been reported. Also, glycine is widely used as a GS linker and does not induce immune responses in commercial products as in Dulaglutide (Cell Biophys. 1993 January-June; 22(103):189-224).

In an exemplary embodiment, the A may be an oligopeptide including 1 to 10 amino acids selected from the group consisting of methionine (Met, M), glycine (Gly, G), and a combination thereof, and preferably, an oligopeptide consisting of 1 to 5 amino acids. For example, the A may have N-terminal sequence of any one selected from the group consisting of methionine, glycine, methionine-methionine, glycine-glycine, methionine-glycine, glycine-methionine, methionine-methionine-methionine, methionine-methionine-glycine, methionine-glycine-methionine, glycine-methionine-methionine, methionine-glycine-glycine, glycine-methionine-glycine, glycine-glycine-methionine, and glycine-glycine-glycine. Specifically, the A may be represented by an amino acid sequence selected from the group consisting of methionine, glycine, methionine-methionine, glycine-glycine, methionine-glycine, glycine-methionine, methionine-methionine-methionine, methionine-methionine-glycine, methionine-glycine-methionine, glycine-methionine-methionine, methionine-glycine-glycine, glycine-methionine-glycine, glycine-glycine-methionine, and glycine-glycine-glycine.

Another aspect of the present invention provides an IL-7 fusion protein, comprising: a first domain comprising a polypeptide having the activity of IL-7 or a similar activity thereof; a second domain including an amino acid sequence having 1 to 10 amino acid residues consisting of methionine, glycine, or a combination thereof; and a third domain which prolongs the half-life of the interleukin-7 fusion protein.

The third domain may be linked to the N-terminal or the C-terminal of the first domain or the second domain. Additionally, the IL-7 including the first domain and the second domain may be linked to both terminals of the third domain.

The third domain may be a fusion partner for increasing in vivo half-life, and preferably, may include any one selected from the group consisting of an Fc region of immunoglobulin or a part thereof, albumin, an albumin-binding polypeptide, Pro/Ala/Ser (PAS), C-terminal peptide (CTP) of β subunit of human chorionic gonadotropin, polyethylene glycol (PEG), long unstructured hydrophilic sequences of amino acids (XTEN), hydroxyethyl starch (HES), an albumin-binding small molecule, and a combination thereof.

When the third domain is an Fc region of immunoglobulin it may be an Fc region of a modified immunoglobulin. In particular, the Fc region of the modified immunoglobulin may be one in which the antibody-dependent cellular cytotoxicity (ADCC) or complement-dependent cytotoxicity (CDC) weakened due to the modification in the binding affinity with the Fc receptor and/or a complement. The modified immunoglobulin may be selected from the group consisting of IgG1, IgG2, IgG3, IgG4, IgA1, IgA2, IgD, IgE and a combination thereof. Specifically, the Fc region of the modified immunoglobulin may include a hinge region, a CH2 domain, and a CH3 domain from the N-terminal to the C-terminal. In particular, the hinge region may include the human IgD hinge region; the CH2 domain may include a part of the amino acid residues of the human IgD and a part of the amino acid residues of the human IgG4 CH2 domain; and the CH3 domain may include a part of the amino acid residues of the human IgG4 CH3 domain.

Additionally, two fusion proteins may form a dimer, for example, when the third domain is an Fc region, the Fc regions may bind to each other and thereby form a dimer.

As used herein, the terms "Fc region", "Fc fragment", or "Fc" refers to a protein which includes the heavy chain constant region 2 (CH2) and the heavy chain constant region 3 (CH3) of immunoglobulin but does not include its variable regions of the heavy chain and the light chain and the light chain constant region (CL1), and it may further include a hinge region of the heavy chain constant region. In the present invention, a hybrid Fc or a hybrid Fc fragment thereof may be called "hFc" or "hyFc."

Additionally, as used herein, the term "an Fc region variant" refers to one which was prepared by substituting a part of the amino acids among the Fc region or by combining the Fc regions of different kinds. The Fc region variant can prevent from being cut off at the hinge region. Specifically, the 144th amino acid and/or 145th amino acid of SEQ ID NO: 9 may be modified. Preferably, the variant may be one, in which the 144th amino acid, K, was substituted with G or S, and one, in which the 145th amino acid, E, was substituted with G or S.

Additionally, the Fc region or the Fc region variant of the modified immunoglobulin may be represented by the following Formula (I):

N'—(Z1)p-Y—Z2-Z3-Z4-C'.  [Formula (I)]

In the above Formula (I),

N' is the N-terminal of a polypeptide and C' is the C-terminal of a polypeptide;

p is an integer of 0 or 1;

Z1 is an amino acid sequence having 5 to 9 consecutive amino acid residues from the amino acid residue at position 98 toward the N-terminal, among the amino acid residues at positions from 90 to 98 of SEQ ID NO: 7;

Y is an amino acid sequence having 5 to 64 consecutive amino acid residues from the amino acid residue at position 162 toward the N-terminal, among the amino acid residues at positions from 99 to 162 of SEQ ID NO: 7;

Z2 is an amino acid sequence having 4 to 37 consecutive amino acid residues from the amino acid residue at position 163 toward the C-terminal, among the amino acid residues at positions from 163 to 199 of SEQ ID NO: 7;

Z3 is an amino acid sequence having 71 to 106 consecutive amino acid residues from the amino acid residue at position 220 toward the N-terminal, among the amino acid residues at positions from 115 to 220 of SEQ ID NO: 8; and Z4 is an amino acid sequence having 80 to 107 consecutive amino acid residues from the amino acid residue at position 221 toward the C-terminal, among the amino acid residues at positions from 221 to 327 of SEQ ID NO: 8.

Additionally, the Fc fragment of the present invention may be in the form of having native sugar chains, increased sugar chains, or decreased sugar chains compared to the native form, or may be in a deglycosylated form. The immunoglobulin Fc sugar chains may be modified by conventional methods such as a chemical method, an enzymatic method, and a genetic engineering method using a microorganism. The removal of sugar chains from an Fc fragment results in a sharp decrease in binding affinity to the C1q part of the first complement component C1, and a decrease or loss of ADCC or CDC, thereby not inducing any unnecessary immune responses in vivo. In this regard, an immunoglobulin Fc region in a deglycosylated or aglycosylated form may be more suitable to the object of the present invention as a drug carrier. As used herein, the term "deglycosylation" refers to an Fc region in which sugars are removed enzymatically from an Fc fragment. Additionally, the term "aglycosylation" means that an Fc fragment is produced in an unglycosylated form by a prokaryote, and preferably in *E. coli*.

Additionally, the Fc region of the modified immunoglobulin may include the amino acid sequence of SEQ ID NO: 9 (hyFc), SEQ ID NO: 10 (hyFcM1), SEQ ID NO: 11 (hyFcM2), SEQ ID NO: 12 (hyFcM3), or SEQ ID NO: 13 (hyFcM4). Additionally, the Fc region of the modified immunoglobulin may include the amino acid sequence of SEQ ID NO: 14 (a non-lytic mouse Fc).

According to the present invention, the Fc region of the modified immunoglobulin may be one described in U.S. Pat. No. 7,867,491, and the production of the Fc region of the modified immunoglobulin may be performed referring to the disclosure in U.S. Pat. No. 7,867,491.

The second domain may be directly linked to the N-terminal of the first domain or linked by a linker. Specifically, the result may be in the form of the second domain—the first domain or the second domain-linker—the first domain.

The third domain may be directly linked to the first domain or the second domain or linked by a linker. Specifically, the result may be in the form of the second domain—the first domain—the third domain, the third domain—the second domain—the first domain, the second domain—the first domain-linker—the third domain, the third domain-linker—the second domain—the first domain, the second domain-linker—the first domain-linker—the third domain, or the third domain-linker—the second domain—the first domain.

When the linker is a peptide linker, the connection may occur in any linking region. They may be coupled using a crosslinking agent known in the art. Examples of the crosslinking agent may include N-hydroxysuccinimide esters such as 1,1-bis(diazoacetyl)-2-phenylethane, glutaraldehyde, and 4-azidosalicylic acid; imidoesters including disuccinimidyl esters such as 3,3'-dithiobis(succinimidylpropionate), and bifunctional maleimides such as bis-N-maleimido-1,8-octane, but is not limited thereto.

Additionally, the linker may be an albumin linker or a peptide linker. The peptide linker may be a peptide of 10 to 20 amino acid residues consisting of Gly and Ser residues.

When the linker is formed by one selected from the group consisting of a chemical bond, the chemical bond may be a disulfide bond, a diamine bond, a sulfide-amine bond, a carboxy-amine bond, an ester bond, and a covalent bond.

In an exemplary embodiment, the modified IL-7 of the present invention may have a structure of A-IL-7 including a polypeptide having the activity of IL-7 or a similar activity thereof and an oligopeptide consisting of 1 to 10 amino acids.

In a specific embodiment, the modified IL-7 may have an amino acid sequence consisting of SEQ ID NOS: 15 to 20. Additionally, the modified IL-7 may have a sequence having a homology of 70%, 75%, 80%, 85%, 90%, 91%, 92%, 93%, 94%, 95%, 96%, 97%, 98%, or 99%, to the amino acid sequences consisting of SEQ ID NOS: 15 to 20.

In another exemplary embodiment, the modified IL-7 or an IL-7 fusion protein of the present invention, which comprising a first domain including a polypeptide having the activity of IL-7 or a similar activity thereof; a second domain comprising an amino acid sequence having 1 to 10 amino acid residues consisting of methionine, glycine, or a combination thereof; and a third domain, which is an Fc region of modified immunoglobulin, coupled to the C-terminal of the first domain.

The IL-7 fusion protein may have an amino acid sequence consisting of SEQ ID NOS: 21 to 25. Additionally, the IL-7 fusion protein may have a sequence having a homology of 70%, 75%, 80%, 85%, 90%, 91%, 92%, 93%, 94%, 95%, 96%, 97%, 98%, or 99%, to the amino acid sequences consisting of SEQ ID NOS: 21 to 25.

Another aspect of the present invention provides an isolated nucleic acid molecule encoding the modified IL-7 or an IL-7 fusion protein.

The nucleic acid molecule may be one encoding the polypeptide having an amino acid sequence selected from the group consisting of SEQ ID NOS: 15 to 25. The nucleic acid molecule may include a polynucleotide sequence selected from the group consisting of SEQ ID NOS: 29 to 39.

The nucleic acid molecule may further include a signal sequence or a leader sequence.

As used herein, the term "signal sequence" refers to a fragment directing the secretion of a biologically active molecule drug and a fusion protein, and it is cut off after being translated in a host cell. The signal sequence of the present invention is a polynucleotide encoding an amino acid sequence initiating the movement of the protein penetrating the endoplasmic reticulum (ER) membrane. The useful signal sequences in the present invention include an antibody light chain signal sequence, e.g., antibody 14.18 (Gillies et al., J. Immunol. Meth 1989. 125:191-202), an antibody heavy chain signal sequence, e.g., MOPC141 an antibody heavy chain signal sequence (Sakano et al., Nature, 1980. 286: 676-683), and other signal sequences know in the art (e.g., see Watson et al., Nucleic Acid Research, 1984. 12:5145-5164).

The characteristics of the signal peptides are well known in the art, and the signal peptides conventionally having 16 to 30 amino acids, but they may include more or less number of amino acid residues. Conventional signal peptides consist of three regions of the basic N-terminal region, a central hydrophobic region, and a more polar C-terminal region.

The central hydrophobic region includes 4 to 12 hydrophobic residues, which immobilize the signal sequence through a membrane lipid bilayer during the translocation of an immature polypeptide. After the initiation, the signal sequence is frequently cut off within the lumen of ER by a cellular enzyme known as a signal peptidase. In particular, the signal sequence may be a secretory signal sequence for tissue plasminogen activation (tPa), signal sequence of herpes simplex virus glycoprotein D (HSV gDs), or a growth hormone. Preferably, the secretory signal sequence used in higher eukaryotic cells including mammals, etc., may be used. Additionally, as the secretory signal sequence, the signal sequence included in the wild type IL-7 may be used or it may be used after substituting with a codon with high expression frequency in a host cell.

Another aspect of the present invention provides an expression vector comprising an isolated nucleic acid molecule encoding the modified IL-7 or an IL-7 fusion protein.

As used herein, the term "vector" is understood as a nucleic acid means which includes a nucleotide sequence that can be introduced into a host cell to be recombined and inserted into the genome of the host cell, or spontaneously replicated as an episome. The vector may include linear nucleic acids, plasmids, phagemids, cosmids, RNA vectors, virus vectors, and analogs thereof. Examples of the virus vectors may include retroviruses, adenoviruses, and adeno-associated viruses, but are not limited thereto.

As used herein, the term "gene expression" or "expression" of a target protein is understood to refer to transcription of a DNA sequence, translation of an mRNA transcript, and secretion of a fusion protein product or a fragment thereof.

As used herein, the term "host cell" refers to a prokaryotic cell and a eukaryotic cell to which a recombinant expression vector can be introduced. As used herein, the terms "transduced", "transformed", and "transfected" refer to the introduction of a nucleic acid (e.g., a vector) into a cell using a technology known in the art.

As used herein, the term "gene expression" or "expression" of a target protein is understood to refer to transcription of a DNA sequence, translation of an mRNA transcript, and secretion of an Fc fusion protein product or an antibody or an antibody fragment thereof.

The useful expression vector may be RcCMV (Invitrogen, Carlsbad) or a variant thereof. The expression vector may include a human cytomegalovirus (CMV) for promoting continuous transcription of a target gene in a mammalian cell and a polyadenylation signal sequence of bovine growth hormone for increasing the stability state of RNA after transcription. In an exemplary embodiment of the present invention, the expression vector is pAD15, which is a modified form of RcCMV.

In another aspect, the present invention provides a host cell including the expression vector. An appropriate host cell can be used for the expression and/or secretion of a target protein, by the transduction or transfection of the DNA sequence of the present invention.

Examples of the appropriate host cell to be used in the present invention may include immortal hybridoma cell, NS/0 myeloma cell, 293 cell, Chinese hamster ovary (CHO) cell, HeLa cell, human amniotic fluid-derived cell (CapT cell) or COS cell.

In still another aspect, the present invention provides a method for producing a protein comprising culturing the transformed cells by the expression vector; and harvesting the modified IL-7 or a fusion protein including IL-7 from the culture or the cells obtained from the culturing process.

The modified IL-7 or a fusion protein including IL-7 may be purified from the culture medium or cell extract. For example, after obtaining the supernatant of the culture medium, in which a recombinant protein was secreted, the supernatant may be concentrated a protein concentration filter available in the commercial market, e.g., an Amicon or Millipore Pellicon ultrafiltration unit. Then, the concentrate may be purified by a method known in the art. For example, the purification may be performed using a matrix coupled to protein A.

In still another aspect, the present invention provides a method for preparing a modified IL-7, including linking an oligopeptide including an amino acid sequence having 1 to 10 amino acid residues consisting of methionine, glycine, or a combination thereof, to the N-terminal of a polypeptide having the activity of IL-7 or a similar activity thereof.

The above preparation method may further include a step of linking a polypeptide consisting of a heterogeneous sequence, and the IL-7 fusion protein can be prepared by the same. In particular, the polypeptide consisting of a heterogeneous sequence may be any one selected from the group consisting of an Fc region of immunoglobulin or a part thereof, albumin, an albumin-binding polypeptide, PAS, CTP of the β subunit of human chorionic gonadotropin, PEG, XTEN, HES, an albumin-binding small molecule, and a combination thereof.

In still another aspect, the present invention provides a method for preparing a modified IL-7, comprising: linking a polynucleotide encoding an oligopeptide including an amino acid sequence having 1 to 10 amino acid residues consisting of methionine, glycine, or a combination thereof, to the N-terminal of a polynucleotide encoding a polypeptide including an amino acid sequence of a first domain having the activity of IL-7 or a similar activity thereof, thereby preparing a linked polynucleotide; and expressing the linked polynucleotide to harvest a modified IL-7 protein.

The above preparation method may further include a step of linking a polynucleotide encoding a polypeptide consisting of a heterogeneous sequence, and the IL-7 fusion protein can be prepared by the same. In particular, the polypeptide consisting of a heterogeneous sequence may be any one selected from the group consisting of an Fc region of immunoglobulin or a part thereof, albumin, an albumin-binding polypeptide, PAS, a CTP of the β subunit of human chorionic gonadotropin, PEG, XTEN, HES, an albumin-binding small molecule, and a combination thereof.

In still another aspect, the present invention provides a pharmaceutical composition for preventing or treating a disease containing the modified IL-7 or an IL-7 fusion protein.

The modified IL-7 or an IL-7 fusion protein of the present invention may be administered for promoting the expansion or survival of naive or pre-existing T-cells or transplanted T-cells, or proliferating the in vitro isolated T-cell aggregates.

The diseases may be a chronic hepatitis, cancer, or an infectious disease. The cancer may be head and neck cancer or uterine cervical cancer, and the chronic hepatitis may be hepatitis B or hepatitis C. Additionally, the infectious disease may be a virus infection, and the virus may be selected from the group consisting of influenza virus, CMV, HSV-1, HSV-2, HIV, HCV, HBV, West Nile fever virus, and Dengue virus. Additionally, the disease may be lymphocytopenia (lymphopenia) or any symptom, disease, and syndrome caused by low numbers of lymphocyte, especially T-cells.

The modified IL-7 or an IL-7 fusion protein of the present invention may further include a pharmaceutically acceptable carrier. The pharmaceutically acceptable carrier may be any non-toxic material which is suitable for the delivery into patients. The carrier may be distilled water, alcohols, fats, waxes, or inactive solids. Additionally, any pharmaceutically acceptable adjuvants (buffering agents, dispersing agents) may also be contained therein.

Additionally, the pharmaceutical composition containing the modified IL-7 or an IL-7 fusion protein of the present invention may be administered to subjects by various methods. For example, the composition may be parenterally administered, e.g., subcutaneously, intramuscularly, or intravenously. The composition may be sterilized by a conventional sterile method. The composition may contain a pharmaceutically acceptable auxiliary material and an adjuvant required for the regulation of physiological conditions such as pH adjustment, a toxicity-adjusting agent, and an analog thereof. Specific examples may include sodium acetate, potassium chloride, calcium chloride, sodium lactate, etc. The concentration of the fusion protein to be included in the formulations may vary widely. For example, the concentration of the fusion protein may be less than about 0.5%, and generally or at least about 1% to as much as 15% to 20%, depending on the weight. The concentration may be selected based on the selected particular administration methods, fluid volumes, viscosities, etc.

In still another aspect, the present invention provides a method for preventing or treating a disease by administering a composition containing the modified IL-7 or an IL-7 fusion protein of the present invention, as an active ingredient.

The method includes administering a therapeutically effective amount of the modified IL-7 or an IL-7 fusion protein of the present invention to a subject in need thereof, which has a health state directly related or unrelated to the target disease. The subject may be a mammal, and preferably, humans.

The composition of the present invention may be administered in any routes. The composition of the present invention may be provided to animals by a direct administration (e.g., locally by an administration via injection, transplantation, or local administration into a tissue region) or system (e.g., parenterally or orally) via an appropriate means. When the composition of the present invention is administered parenterally by intravenously, subcutaneously, intraocularly, intraperitoneally, intramuscularly, orally, intrarectally, intraorbitally, intracerebrally, intracranially, intraspinally, intraventricularly, intrathecally, intracistenally, intracapsularly, intranasally, or aerosol administration, the composition preferably contains an aqueous or physiologically applicable suspension of body fluids or a part of the solution thereof. As such, the physiologically acceptable carrier or transporter can be added into the composition and delivered to patients, and this does not cause a negative effect on the electrolyte and/or volume balance of patients. Accordingly, the physiologically acceptable carrier or transporter may be a physiological saline.

Additionally, a DNA construct (or a genomic construct) including a nucleic acid including the modified IL-7 or an IL-7 fusion protein of the present invention may be used as a part of the gene therapy protocol.

In the present invention, for reconstituting or complementing the functions of a desired protein, an expression vector capable of expressing a fusion protein in a particular cell may be administered along with any biologically effective carrier. This may be any formulation or composition that can efficiently deliver a gene encoding a desired protein or an IL-7 fusion protein into a cell in vivo.

For the purpose of gene therapy using a nucleic acid encoding the modified IL-7 or an IL-7 fusion protein, a subject gene may be inserted into a virus vector, a recombinant bacteria plasmid, or a recombinant eukaryotic plasmid. The virus vector may include a recombinant retrovirus, an adenovirus, an adeno-associated virus, and herpes simplex virus-1, etc. The administration dose of the nucleic acid encoding the fusion protein of the present invention for gene therapy, for humans, may be in the range of 0.1 mg to 200 mg. In an exemplary embodiment, the preferred dose of the nucleic acid encoding the fusion protein of the present invention, for humans, may be in the range of 0.6 mg to 100 mg. In another exemplary embodiment, the preferred dose of the nucleic acid encoding the fusion protein of the present invention, for humans, may be in the range of 1.2 mg to 50 mg.

The unit dose of the modified IL-7 or an IL-7 fusion protein of the present invention may be in the range of 0.001 mg/kg to 10 mg/kg. In an exemplary embodiment, the unit dose of the modified IL-7 or an IL-7 fusion protein may be in the range of 0.01 mg/kg to 2 mg/kg. In another exemplary embodiment, the unit dose of the protein, for humans, may be in the range of 0.02 mg/kg to 1 mg/kg. The unit dose may vary depending on the subject diseases for treatment and the presence of adverse effects. The administration of the modified IL-7 protein may be performed by periodic bolus injections or external reservoirs (e.g., intravenous bags) or by continuous intravenous, subcutaneous, or intraperitoneal administration from the internal (e.g., biocorrosive implants).

The modified IL-7 or an IL-7 fusion protein of the present invention may be administered in combination with other drug(s) or physiologically active material(s) which have a preventative or treating effect on the disease to be prevented or treated, or may be formulated into a combined preparation in combination with other drug(s), for example, may be administered in combination with an immunostimulant such as a hematopoietic growth factor, a cytokine, an antigens, and an adjuvant. The hematopoietic growth factor may be a stem cell factor (SCF), a G-CSF, a GM-CSF, or an Flt-3 ligand. The cytokine may be γ interferon, IL-2, IL-15, IL-21, IL-12, RANTES, or B7-1.

The method of preventing or treating diseases using the composition containing the modified IL-7 or an IL-7 fusion protein of the present invention may also include to administer in combination with other drug(s) or physiologically active material(s), and the routes for the combined administration, administration period, and dose may be determined depending on the types of diseases, health state of the patient, purpose of treatment or prevention, and other drug (s) or physiologically active material(s) to be administered in combination.

Hereinafter, the present invention is explained in detail by Examples. The following Examples are intended to further illustrate the present invention without limiting its scope.

Example 1. Preparation of a Modified IL-7 Protein in which an Oligopeptide is Coupled to IL-7

A modified IL-7, in which an oligopeptide is coupled to the N-terminal of IL-7 was prepared. For the IL-7, the sequence of human IL-7 (SEQ ID NO: 1) was used and, as an oligopeptide, methionine (M), glycine (G), MM, GG, MG, GM, MMM, MMG, MGM, GMM, MGG, GMG, GGM, GGG, DDD, or MMMM sequence was used.

As shown in FIG. 1A, various forms of the modified IL-7 having the structure of the 'A'-IL-7 were prepared. In this Example, methionine (M), glycine (G), MM, GG, MG, GM, MMM, MMG, MGM, GMM, MGG, GMG, GGM, GGG, DDD, or MMMM sequence was used as the 2nd domain (oligopeptide, 'A'). For the IL-7 as the 1st domain being fused to the oligopeptide, a nucleic acid sequence of SEQ ID NO: 28 was used. An entire nucleic acid sequence in the form where the IL-7 was fused to the oligopeptide was obtained and then inserted into an expression vector. As a negative control, an IL-7 protein without having the oligopeptide modification was prepared in the same manner.

An expression vector including the A-IL-7 gene was transfected into HEK293 cell. Based on the 300 mL of a suspension culture, a polyplex was prepared using 208.3 ug of DNA and 416.6 ug (μL) of polyethylenimine (PEI)(w/w), and then transfected into the HEK293F cell. Six days after the transfection, the cell culture was obtained and subjected to western blot and thereby the expression rate of the target protein was evaluated. Then, the culture was centrifuged at 8,000 rpm for 30 minutes and the culture debris was removed and filtered using a bottle top filter with a pore size of 0.22 um. As a result, the culture liquid containing the modified IL-7 of M-IL-7, G-IL-7, MM-IL-7, GG-IL-7, MG-IL-7, GM-IL-7, MMM-IL-7, MMG-IL-7, MGM-IL-7, GMM-IL-7, MGG-IL-7, GMG-IL-7, GGM-IL-7, GGG-IL-7, DDD-IL-7, and MMMM-IL-7 was obtained.

Example 2. Preparation of an IL-7 Fusion Protein in which an Fc Region is Coupled to the C-Terminal of IL-7

An IL-7 fusion protein, i.e., the second domain—the first domain—the third domain, in which a polypeptide consisting of a heterogeneous amino acid sequence was further coupled to the C-terminal of a modified IL-7 was prepared. For the first domain, the sequence of human IL-7 (SEQ ID NO: 1) was used, and as the second domain, M, G, MM, GG, MG, GM, MMM, MMG, MGM, GMM, MGG, GMG, GGM, GGG, DDD, or MMMM sequence was used. For the third domain, the sequence of the Fc region (SEQ ID NO: 9 or 14) was used.

Figure 1B:
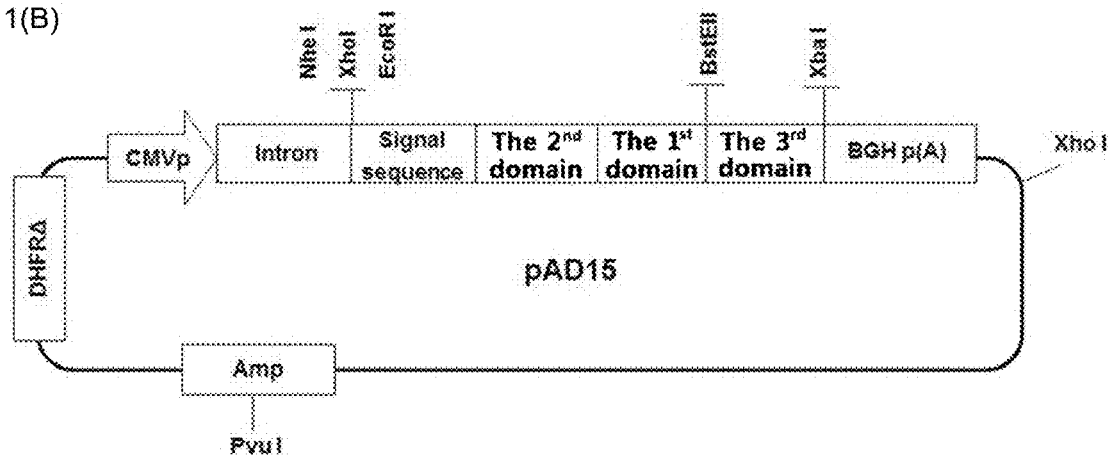

As shown in FIG. 1B, various forms of the IL-7 fusion proteins consisting of the second domain, the first domain and the third domain were prepared. In this Example, as the second domain, methionine (M), glycine (G), MM, GG, MG, GM, MMM, MMG, MGM, GMM, MGG, GMG, GGM, GGG, DDD, or MMMM sequence was used; as the first domain, the human IL-7 was used; and as the third domain, hybrid Fc (hFc, hyFc) or mouse non-lytic Fc was used.

In particular, for the hybrid Fc, the hFc (hybrid Fc) disclosed in U.S. Pat. No. 7,867,491 was used. The hFc can be coupled to a physiologically active protein and thereby exhibit an excellent in vivo half-life compared to the Fc region of the existing modified immunoglobulin.

A gene expression vector was prepared in the same manner as in Example 1 and transfected, and the cells were cultured to prepare a culture liquid containing various forms of IL-7 fusion proteins. As a result, a culture liquid containing G-IL-7-hyFc, M-IL-7-hyFc, MM-IL-7-hyFc, GG-IL-7-hyFc, MG-IL-7-hyFc, GM-IL-7-hyFc, MMM-IL-7-hyFc, MMG-IL-7-hyFc, MGM-IL-7-hyFc, GMM-IL-7-hyFc, MGG-IL-7-hyFc, GMG-IL-7-hyFc, GGM-IL-7-hyFc, GGG-IL-7-hyFc, DDD-IL-7-hyFc, or MMMM-IL-7-hyFc protein was obtained. Additionally, as a control group, a culture liquid containing an IL-7-hyFc protein consisting of the first domain and the third domain was produced.

Example 3. Production and Purification of Modified IL-7 and Modified IL-7 Fusion Protein The amount of production of the modified IL-7 proteins and the modified IL-7 fusion proteins produced in Examples above were compared. For each of the fusion proteins, the amount of the proteins in the culture liquid and the amount of proteins present in the cells were measured.

The concentration of the proteins secreted extracellularly was measured by obtaining the cell culture liquid, and the amount of the proteins in the cell was obtained by cell lysis, and the concentration was measured by ELISA method. For the primary antibody, human IL-7-specific antibody (Southern Biotech, Cat#10122-01) was used, and as the secondary antibody, Biotin (BD, Cat#554494) and Streptavidin-HRP (BD, Cat#554066) were used.

The result of the change in the productivity according to the presence of coupling of an oligopeptide to the N-terminal is shown in Table 2 below.

TABLE 2

| The Second Domain | The First Domain | The Third Domain | Average Concentration A in Culture Liquid (ug/mL) | Intracellular Concentration B (ug/mL) | Total Production (A + B) (ug/mL) | Relative Total Production (%) |
|---|---|---|---|---|---|---|
| (non) | IL-7 | (non) | 53.2 | 3.8 | 57.0 | 100 |
| DDD | IL-7 | (non) | 37.3 | 3.0 | 40.3 | 71 |
| MGM | IL-7 | (non) | 63.0 | 5.9 | 68.9 | 121 |
| MGM | IL-7 | hFc | 154.8 | 5.3 | 160.1 | 281 |

As a result, as shown in Table 2, the amount of production of the MGM-IL-7 was increased, compared to IL-7, to which an oligopeptide was not coupled or the DDD-IL-7, to which an amino acid other than methionine and glycine was coupled.

Additionally, when hyFc was further fused to the C-terminal of the modified IL-7, the protein produced was shown to be present at high concentration and the relative total production showed about a 2.8-fold increase.

Example 4. Evaluation of Productivity of the Prepared Modified IL-7 and IL-7 Fusion Proteins Among the gene constructs prepared in Example 2, each of the genes of the IL-7-hyFc and MGM-IL-7-hyFc proteins was inserted into pAD15 vector. Then, the pAD15 vector was transfected into the CHO DG44 cell (Columbia University, USA) in adhesion or suspension culture by electroporation method. In the case of adhesion culture, the medium was replaced with a medium containing 10% dFBS (Gibco, USA, 30067-334), MEM alpha (Gibco, 12561, USA, Cat. No. 12561-049), HT (5-hydroxytrypamine, Gibco, USA, 11067-030), five hours after the electroporation. Forty eight hours after the transfection, the medium was replaced with MEM alpha medium containing 10% dFBS without HT, and HT selection was performed. The clones completed with HT selection were subjected to MTX amplification for the amplification of productivity, and the cells were subcultured 2 or 3 times for the stabilization of the cells.

The unit productivity (pg/cell/day, pcd, p/c/d) of the modified IL-7(A-IL-7) and IL-7 fusion protein (A-IL-7-hyFc) was evaluated during the HT selection and MTX amplification. During the subculture, the culture supernatant was recovered and the number of cells was measured, and the amount of each protein was measured from the supernatant using the human IgG ELISA kit (Bethyl, USA). The unit productivity was calculated according to Equation 1 below and the producing cell line was evaluated (pg/cell/day, pcd):

$$\text{Unit Productivity (pg/cell/day, } pcd\text{)} = \frac{\frac{\text{Culture Productivity}}{(\text{pg/mL} \times \text{Total Culture Volume})}}{\frac{\text{Number of Survived Cells}}{(\text{cells}/T25) \times \text{Days of Culture (day)}}}$$ [Equation 1]

Limiting dilution cloning (LDC) was performed using the clones selected by the evaluation of unit productivity, and as a result, the single cell clones with increased productivity were selected. The selected single cell clones were cultured as a suspension cell line using serum-free medium. The long term stability (LTS) test was evaluated by setting a single subculture as 3 days and subculturing 35 times, and the results are shown in FIGS. 2A and 2B.

As shown in FIG. 2A, the IL-7 fusion protein, in which an oligopeptide was not coupled to the N-terminal, did not show an increase in its productivity according to increase of MTX concentration. In this regard, MTX treatment was performed up to the 4 times for further improvement of the productivity, but it was not effective. However, as shown in FIG. 2B, the IL-7 fusion protein (MGM-IL-7-hyFc), in which an oligopeptide was coupled to the N-terminal, showed a significant increase in productivity in an MTX concentration-dependent manner. After the LDL performance, the productivity of the protein was shown to be about 28 pg/cell/day and about 16 ug/mL.

From the above, it was confirmed that the coupling of an oligopeptide to the IL-7 protein could exhibit an excellent effect on the improvement of the productivity of the prepared recombinant IL-7.

Example 5. Confirmation of Stability of the Prepared Modified IL-7 and IL-7 Fusion Proteins The culture liquid samples of the IL-7-hyFc and MGM-IL-7-hyFc proteins acquired from the Examples above were purified, and the purified proteins were subjected to size-exclusion (SE) HPLC, and the protein stability according to the concentration of sodium chloride was confirmed.

First, the IL-7-hyFc and MGM-IL-7-hyFc proteins were diluted in a buffer to a concentration of 1 mg/mL. The diluted proteins were filtrated using a 1 mL syringe and a 0.2 um filter and added into vials. The vials were inserted into an insert and closed by the vial caps. The proteins were injected into the SE-HPLC system in an amount of 20 μL, respectively. The SE-HPLC was performed under the following conditions, and the purity was confirmed through the values of the peaks obtained thereof.

Figure 3:
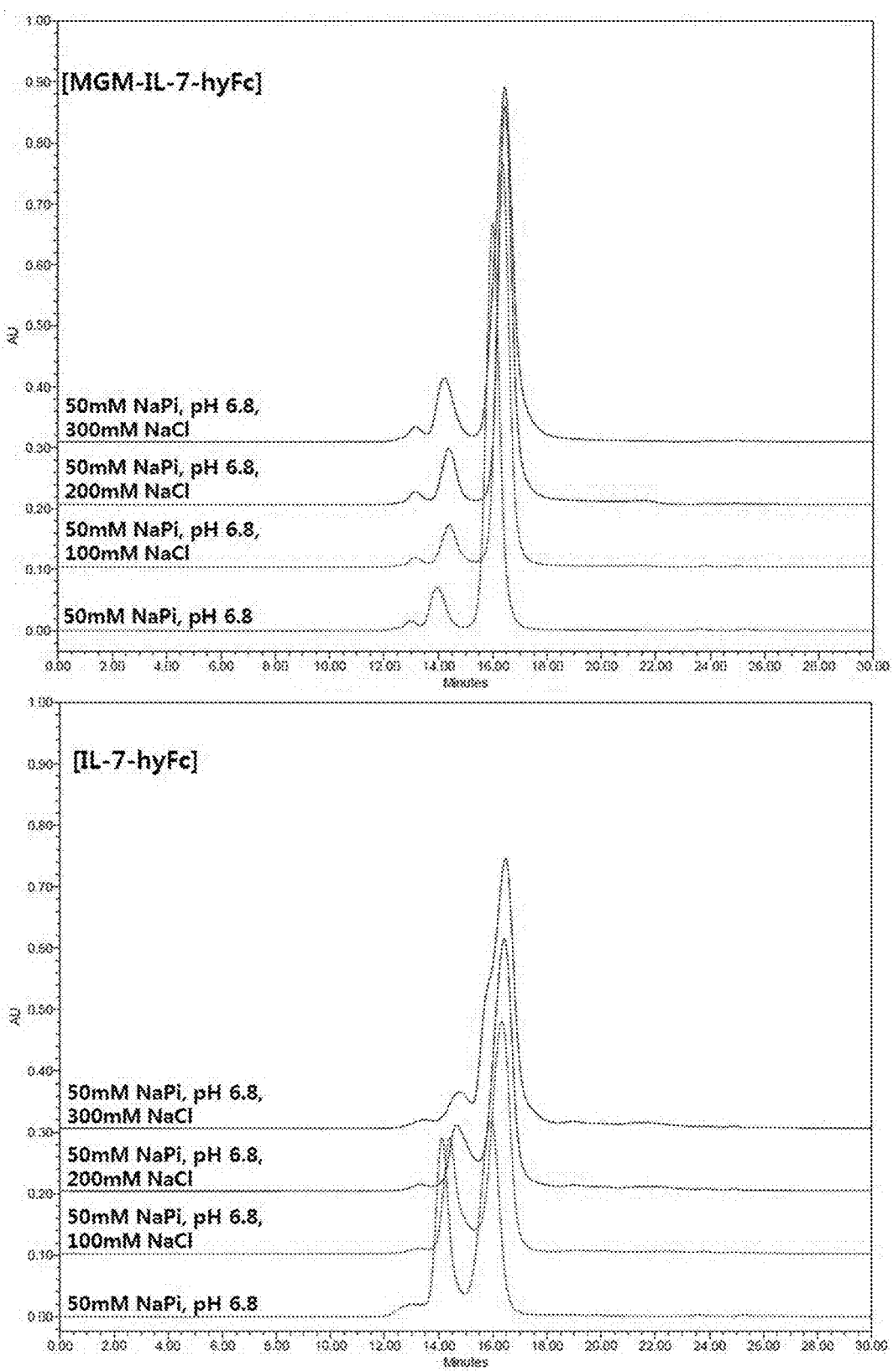
FIG. 3 shows the result of comparing the stability between IL-7-hyFc and MGM-IL-7-hyFc including the same according to the various concentrations of sodium chloride.

<SE-HPLC Performing Conditions>
Column: TSK-GEL G3000SWxL column (7.8 mm×300 mm) (Tosoh, Japan)
Column Temperature: 25° C.
Mobile Phase: a mixed buffer of 50 mM sodium phosphate and 100 mM, 200 mM, or 300 mM sodium chloride (pH 6.8)
Flow rate: 0.6 mL/min
Analysis Time: 40 min
Analysis Method: isocratic method As a result, as shown in FIG. 3, the MGM-IL-7-hyFc protein showed a stable pattern although the concentration of sodium chloride changed, compared to the IL-7-hyFc protein.

Example 6. Confirmation of Native-PAGE of the Prepared Modified IL-7 and IL-7 Fusion Proteins The difference in stability between the modified IL-7 fusion protein and the IL-7 fusion protein according to the concentration of sodium chloride confirmed in Example 5 was reconfirmed, as follows.

Specifically, native-PAGE was performed according to the conditions described in Table 3 below using IL-7-hyFc and MGM-IL-7-hyFc prepared under the same conditions as in the Examples above. G-CSF-hyFc was used as a control group.

TABLE 3

| | |
|---|---|
| Gel | Novex 8-16% Tris-glycine gel (1.5 mm) |
| Sample Buffer | Tris-glycine Native Sample Buffer (2x) (Invitrogen, LC2673) |
| Running Buffer | Tris-glycine Native Running Buffer (10x) (Invitrogen, LC2672) |
| Running Condition | 150 V, 5 hr 35 min (in 5° C. cold room) |
| Amount of Loading | 7 ug/well |

Figure 4:
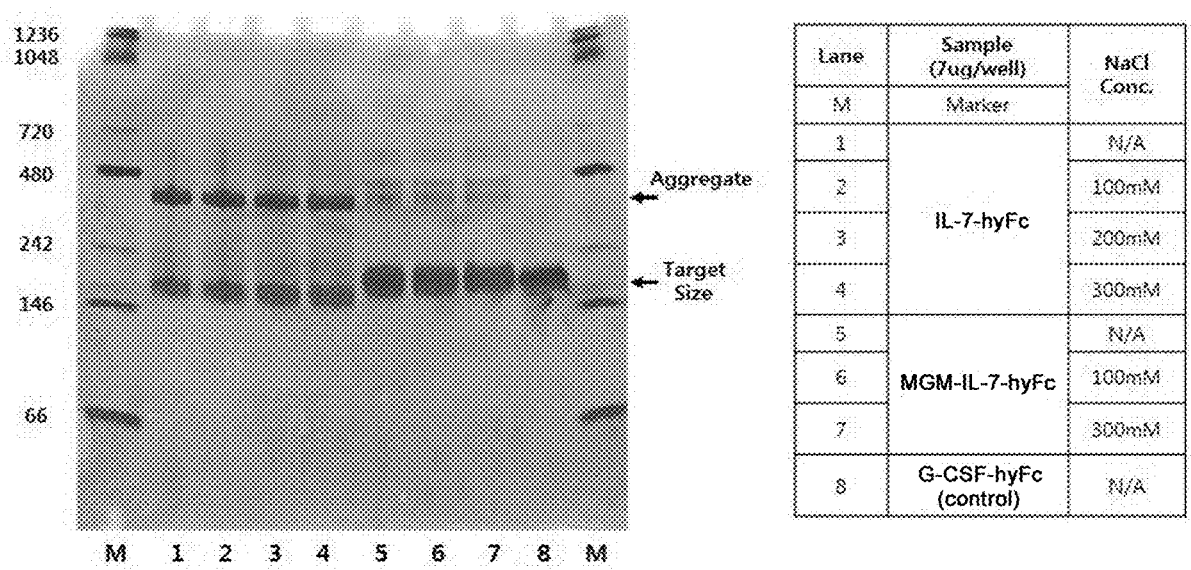
FIG. 4 shows the result of comparing the native-PAGE between IL-7-hyFc and MGM-IL-7-hyFc according to the various concentrations of sodium chloride.

As a result as shown in FIG. 4, there was no aggregate occurred in the MGM-IL-7-hyFc protein, compared to the IL-7-hyFc protein, which is consistent with the result of SE-HPLC.

Example 7. Analysis of Culture Samples of the Prepared Modified IL-7 and IL-7 Fusion Protein The cell lines with the highest productivity among the cell lines, which can produce IL-7-hyFc or MGM-IL-7-hyFc protein, were selected according to the results of Examples 5 and 6. Then, the subcultured culture liquid was obtained and the SE-HPLC was performed by the same method under the same conditions as in Example 5.

Figure 5A:
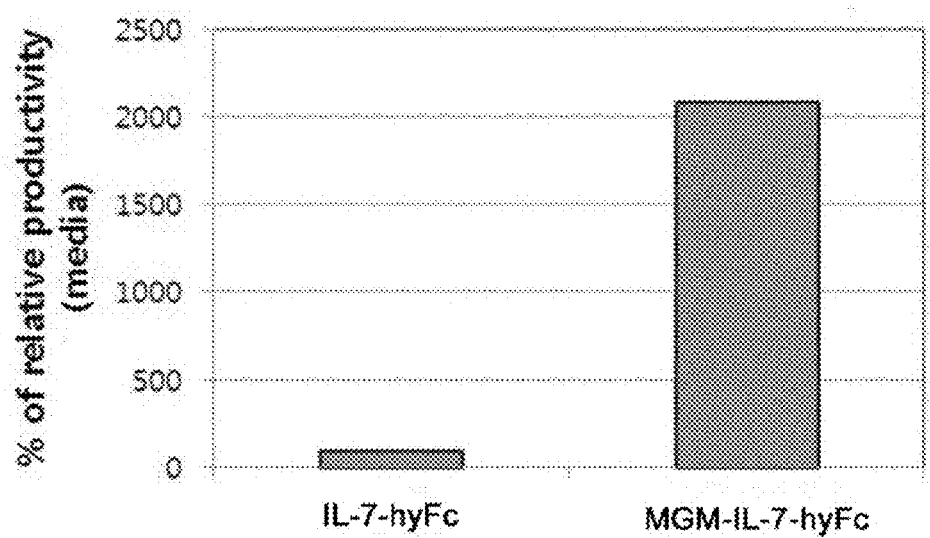
FIGS. 5(A) and 5(B) show the result of comparing relative productivity (FIG. 5A) and purity (FIG. 5B) of the prepared IL-7 fusion proteins, respectively.
Figure 5B:
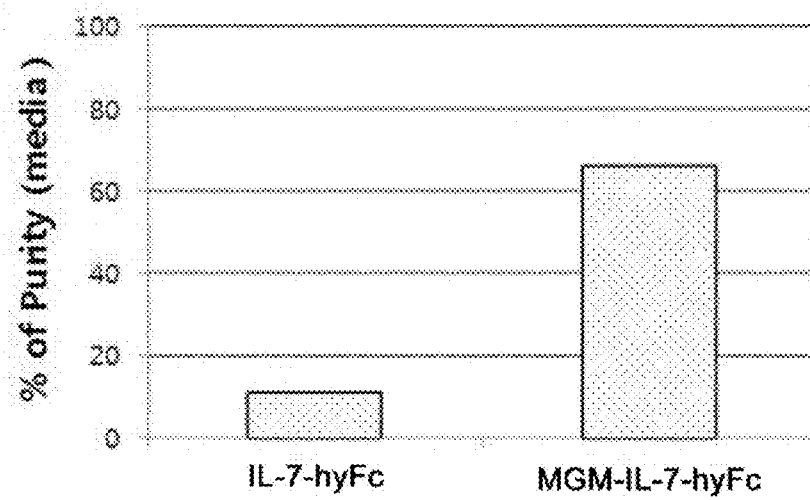

As a result, as shown in FIG. 5A, the relative productivity of the MGM-IL-7-hyFc was 2,091%, which was about a 21-fold increase, compared to the amount of the produced IL-7-hyFc protein, which was set as 100%. Additionally, when the amount of the target protein was compared relative to the total proteins produced by each host cell, while the purity of the IL-7-hyFc was about 11.3%, that of the MGM-IL-7-hyFc protein was about 66.4% thus showing about a 6-fold increase (FIG. 5B).

From the result, it was confirmed that coupling an oligopeptide to the IL-7 protein could exhibit an excellent effect on the improvement of purity and productivity of the prepared recombinant IL-7 fusion protein.

Example 8. Pharmacokinetic Profiles of the Prepared Modified IL-7 and IL-7 Fusion Protein The pharmacokinetic profiles (PK) were confirmed by comparing the half-life and the area under the curve (AUC) of the prepared IL-7-hyFc and MGM-IL-7-hyFc recombinant protein.

First, male Sprague Dawley (SD) rats (5 rats/group) were subcutaneously administered with each of the recombinant protein in an amount of 0.2 mg/kg, respectively. Blood samples were collected before the administration and at 4, 8, 12, 24, 48, 72, 96, 120, 144, and 168 hours after the administration, and stored at room temperature for 30 minutes to aggregate the blood samples. The aggregated blood samples were centrifuged at 3,000 rpm for 10 minutes and the blood serum of each sample was obtained and stored in a deep-freezer.

Figure 6:
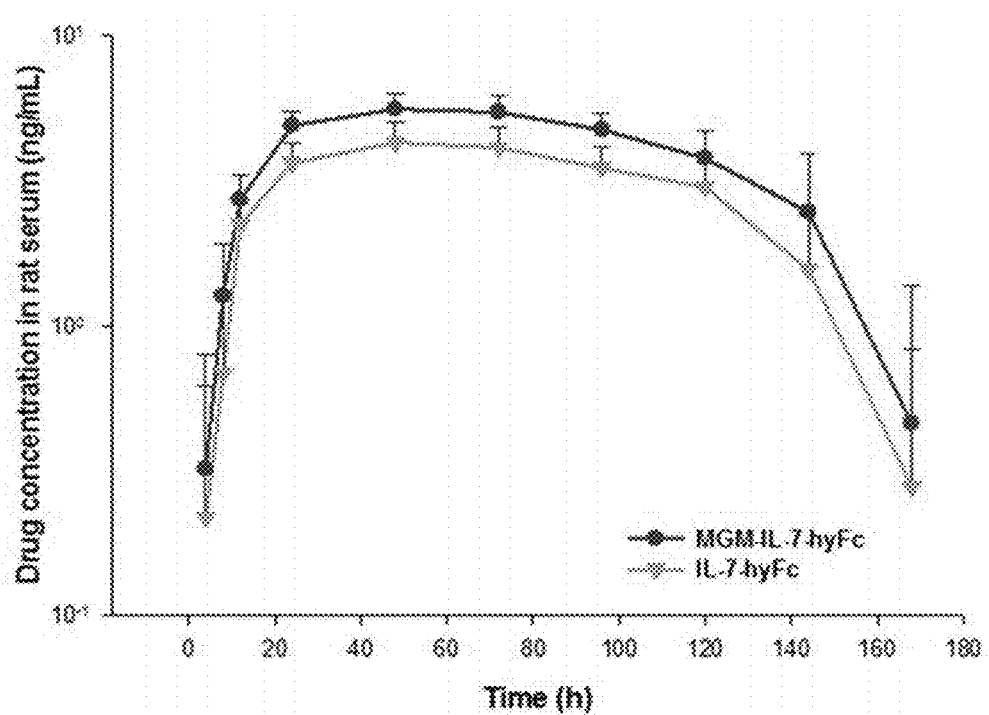
FIG. 6 shows a graph illustrating the serum drug level according to time after subcutaneous administration of the prepared IL-7 fusion proteins to an SD rat model.

The samples were analyzed by a test method designed to specifically detect the intact form of the recombinant protein in which no cleavage occurred. Specifically, it is a method for detecting a target protein using the secondary antibody (Southern Biotech, Cat#9190-05), to which HRP being coupled to the human immunoglobulin G4 (IgG4) of mouse origin is conjugated, after loading a bio-sample containing the prepared recombinant protein into a plate coated with a capture antibody of mouse origin (R&D, Cat# MAB207), which is coupled to the human IL-7. The samples were quantitated by a 10-fold dilution with 1×PBS containing 10% skim milk to be analyzed in a linear position of a standard curve. The results are illustrated in FIG. 6, in terms of the protein amount remaining in the blood per each time point and the drug concentration area under the curve.

As a result, the IL-7-hyFc and MGM-IL-7-hyFc recombinant proteins showed similar AUC values (about a 1.2-fold). As such, it was confirmed that the fusion of the oligopeptide, which is the second domain, causes no change in pharmacokinetics of the first domain. Therefore, the MGM-IL-7-hyFc recombinant protein and the IL-7-hyFc recombinant protein could exhibit similar pharmacokinetic profile in vivo.

Example 9. Immunogenicity of the Prepared Modified IL-7 and IL-7 Fusion Proteins The anti-drug antibody (ADA) producing ability according to the administration of the IL-7-hyFc and MGM-IL-7-hyFc recombinant proteins prepared above was compared, and thereby the antigenicity of each IL-7 fusion protein was examined.

First, the blood samples obtained in the same manner as described in Example 8 were loaded into the plate, which was coated with the IL-7-hyFc or MGM-IL-7-hyFc recombinant proteins in an amount of 0.2 ug/well. Then, the samples were analyzed using the test method designed to detect the ADA in rats using the rat immunoglobulin antibody (Southern Biotech, Cat#1031-05), to which HRP was conjugated.

In particular, the samples were analyzed by diluting them until the reaction of the ADA became the same as the reaction of the normal rat sera (Negative Cut Off; NCO), and the reaction of the samples according to the dilution fold was measured by optical density. The results are illustrated in FIG. 7.

Figure 7:
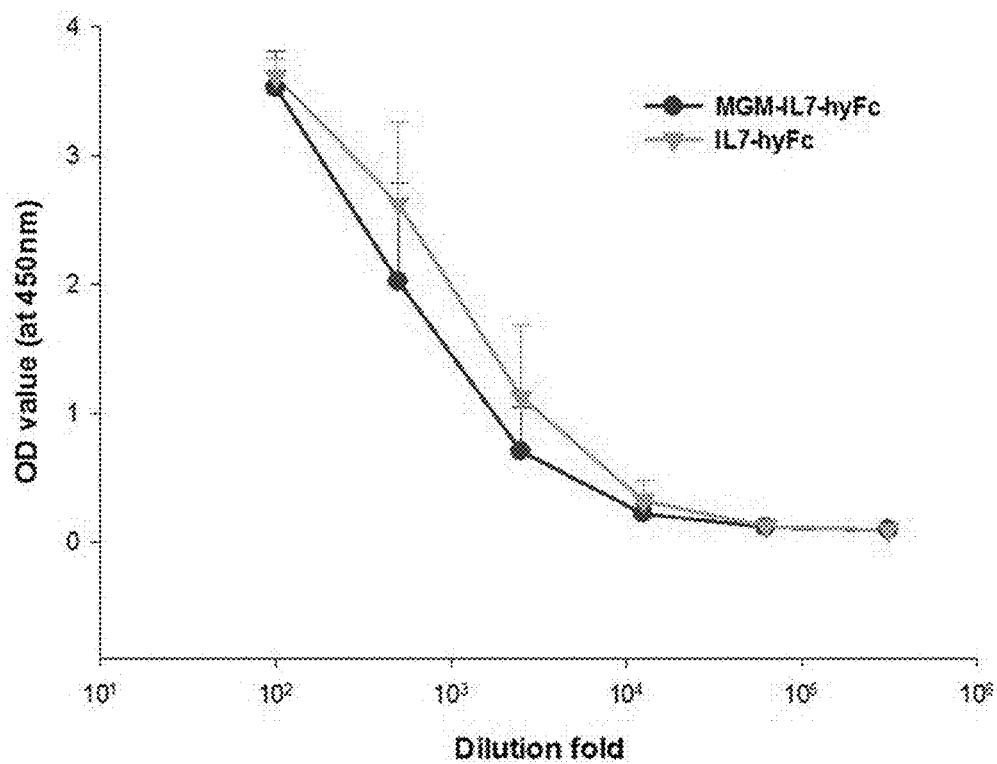
FIG. 7 shows the result of illustrating the production level of anti-drug antibody (ADA) according to each protein administration after subcutaneous administration of the prepared IL-7 fusion proteins to an SD rat model.

As a result, as shown in FIG. 7, the dilution fold required for the IL-7-hyFc and the MGM-IL-7-hyFc to arrive at the negative cut off (NCO) was similar. From the result, it was confirmed that the fusion of the oligopeptide, which is the second domain, does not increase antigenicity.

Example 10. Pharmacodynamic Profile of the Prepared Modified IL-7 and IL-7 Fusion Proteins The number of white blood cells (WBC) according to the administration of the MGM-IL-7-hyFc and IL-7-hyFc recombinant proteins prepared above was compared, and the pharmacodynamic profile for each of the protein was confirmed.

First, male SD rats (5 rats/group) were subcutaneously administered with each protein in an amount of 0.2 mg/kg. Then, blood samples were collected from the rats before the administration and on the 1st, the 2nd, and the 3rd week after the administration. To prevent the aggregation of the blood samples, the samples were obtained in EDTA-treated tubes, mixed for 5 minutes and stabilized, and the number of WBC was analyzed by complete blood count (CBC) analysis.

Figure 8:
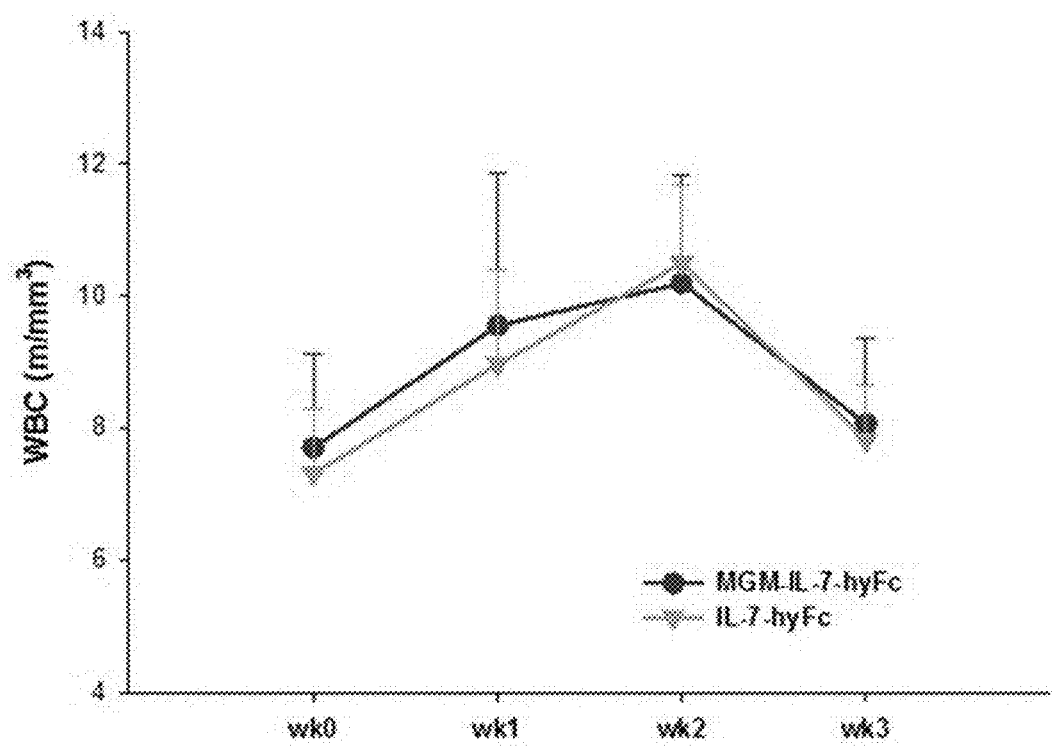
FIG. 8 shows a graph illustrating the effect of increasing the number of white blood cells (WBC) according to time after subcutaneous administration of the prepared IL-7 fusion proteins to an SD rat model.

As a result, as shown in FIG. 8, the IL-7-hyFc and MGM-IL-7-hyFc recombinant proteins increased the number of WBC to the highest level in a similar manner on the 2nd week after the administration. That is, there is no pharmacodynamics change by the fusion of the oligopeptide, which is the second domain. Accordingly, it was confirmed that the IL-7-hyFc and MGM-IL-7-hyFc recombinant proteins can exhibit similar pharmacodynamics profiles.

Example 11. Comparison of In Vitro Activity of the Prepared Modified IL-7 and IL-7 Fusion Proteins The analysis of bioactivity was performed using 2E8 cells (ATCC, TIB-239), which are murine immature B lymphocytes.

First, the cells were seeded into a 96-well plate (1×105 cells/50 μL/well), and the MGM-IL-7-hyFc was stepwise diluted at a concentration of 750 pM to 2.93 pM and treated on the wells. The cells were cultured in an incubator (37° C., 5% CO2) for 70 hours, treated with MTS at a concentration of 20 μL/well, and cultured again in the incubator (37° C., 5% CO2) for 4 hours. Then, the absorbance was measured at 490 nm. In particular, WHO international standard human IL-7 (NIBSC code: 90/530, 100,000 unit) was used as the control group. The calibration curve according to the concentration of the MGM-IL-7-hyFc treatment was created (4-parameter fit) and the result of analysis is shown in FIG. 9.

Figure 9:
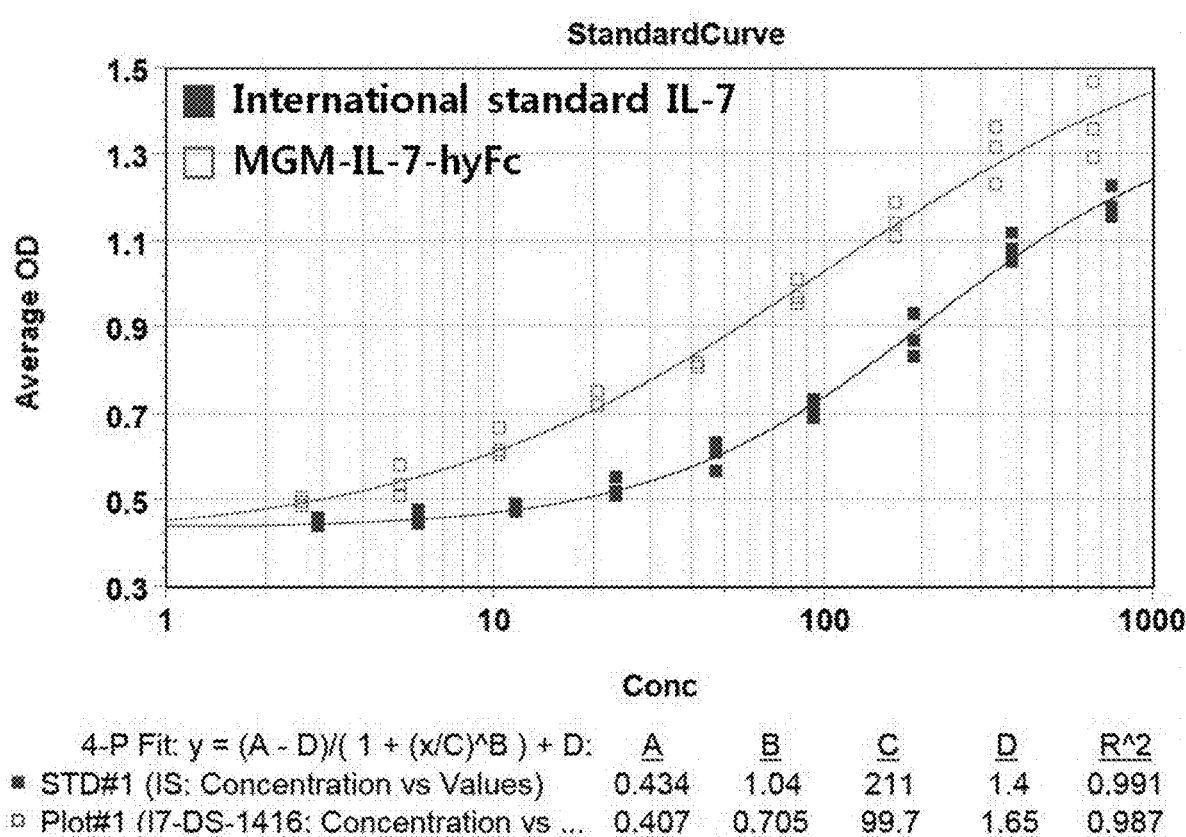
FIG. 9 shows the result of comparing the activity between the prepared IL-7 fusion proteins and the standard material.

As a result, as shown in FIG. 9, based on the international standard 100,000 unit, the log EC50-based activity of the MGM-IL-7-hyFc was shown to be 126,000 unit, and the PLA-based activity was shown to be 371,000 unit. This indicates that, considering the number of molecules of IL-7, the activity of the MGM-IL-7-hyFc is similar to or higher than that of the international standard human IL-7.

Example 12. Prevention and Treatment Effect of the Prepared Modified IL-7 Fusion Protein in a Model Infected with a Lethal Dose of Influenza The mouse model with a lethal dose of influenza was prepared by anesthetizing followed by the administration with 3LD50 H5N2 virus (A/Aquatic bird/Korea/W81/2005) through nasal cavity. Generally, virus-infected mice begin to lose their body weight from 2~3 days and die from a week and thereafter. The thus-prepared disease model was administered with the IL-7 recombinant proteins prepared in Examples 2 and 4 through nasal cavity, and the IL-7-mFc (mouse Fc) (SEQ ID NO: 27) was used as a control group.

In particular, G-CSF can inhibit the early stage influenza infection and proliferate neutrophils thereby promoting immune response. So, G-CSF-hyFc was used as another experimental group.

Six mice were used per each experimental group, and IL-7-mFc (IL-7-mouse Fc), MGM-IL-7-hyFc, or G-CSF-hyFc was administered through nasal cavity 14 days before the infection with a lethal dose of influenza. Then, 3LD50 H5N2 virus was administered and the body weight and survival rate were observed for 20 days.

Figure 10A:
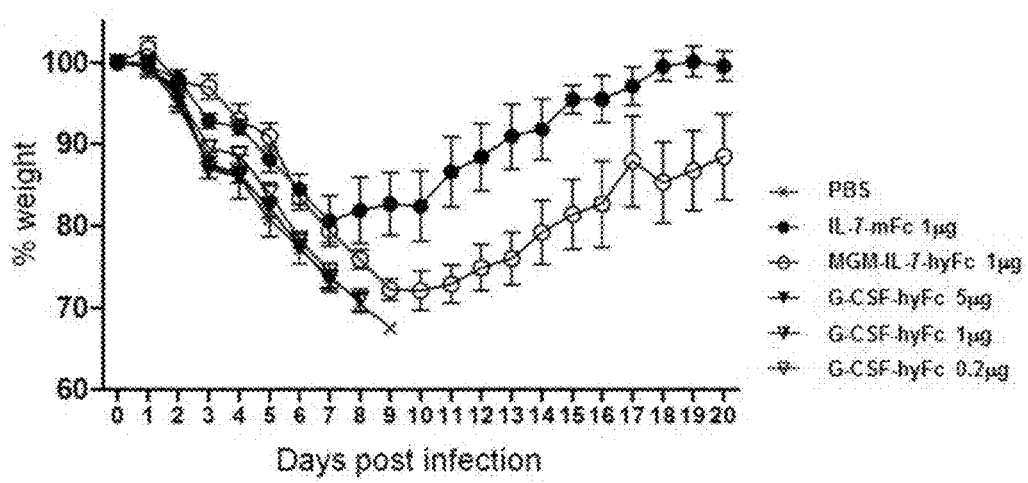
FIGS. 10(A) and 10(B) are graphs illustrating the change in body weight (FIG. 10(A)) and the change in survival rate (FIG. 10(B)), in a lethal influenza disease model, according to the administration of the prepared IL-7 fusion proteins.
Figure 10B:
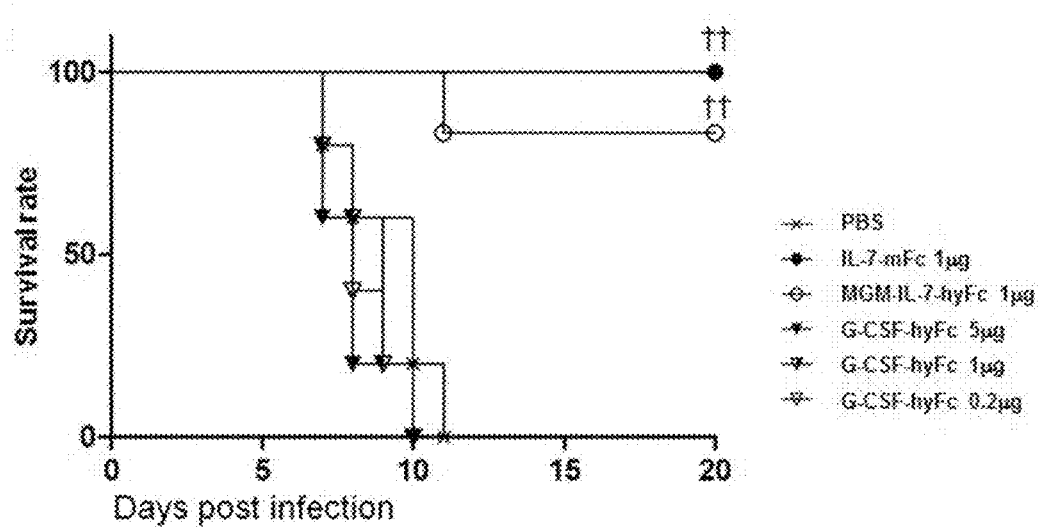

As a result, as shown in FIG. 10A, the body weight began to decrease in all groups. However, the gap of body weight reduction was gradually decreased in the group treated with IL-7-mFc and the group treated with MGM-IL-7-hyFc and gradually recovered body weight, and their survival rate was high unlike that of the control group. As shown in FIG. 10B, the group treated with IL-7-mFc survived 100% and the group treated with MGM-IL-7-hyFc showed a 83% survival rate.

The reason that the effect of MGM-IL-7-hyFc is observed slightly lower than that of IL-7-mFc appears to be due to the difference between species. That is, in the in vivo system of a mouse, the human-derive Fc has lower function than that of a mouse-derived Fc.

Meanwhile, the group treated with PBS or G-CSF-hyFc showed a very low effect and thus the survival rate of the mice infected with a lethal dose of influenza in 10 days was 0%.

In conclusion, the MGM-IL-7-hyFc recombinant proteins showed a strong effect in an influenza model, but G-CSF-hyFc did not, indicating that MGM-IL-7 is very effective in influenza.

Example 13. Treatment Effect of the Prepared Modified IL-7 Fusion Protein in a Model with TC-1 Cancer Disease In order to prepare a disease model with endometrial cancer, mice were administered intraperitoneally with 3 mg of Depo-Provera to adjust the period of their menstruation. In 4 days, the mice were administered with nonoxynol-9 (N9, USP, Cat. No. 1467950) into the vagina to stimulate the vagina tissue, and the remaining N9 was removed by washing with PBS. Then, for the transplant of the cancer cells into the uterus, 1×105 TC-1 cell (Dr. Jae-Tae LEE, School of Medicine, Kyungpook National University) were administered, and then 1 day thereafter, 1 ug of MGM-IL-7-hyFc was administered into the uterine cervix.

Figure 11:
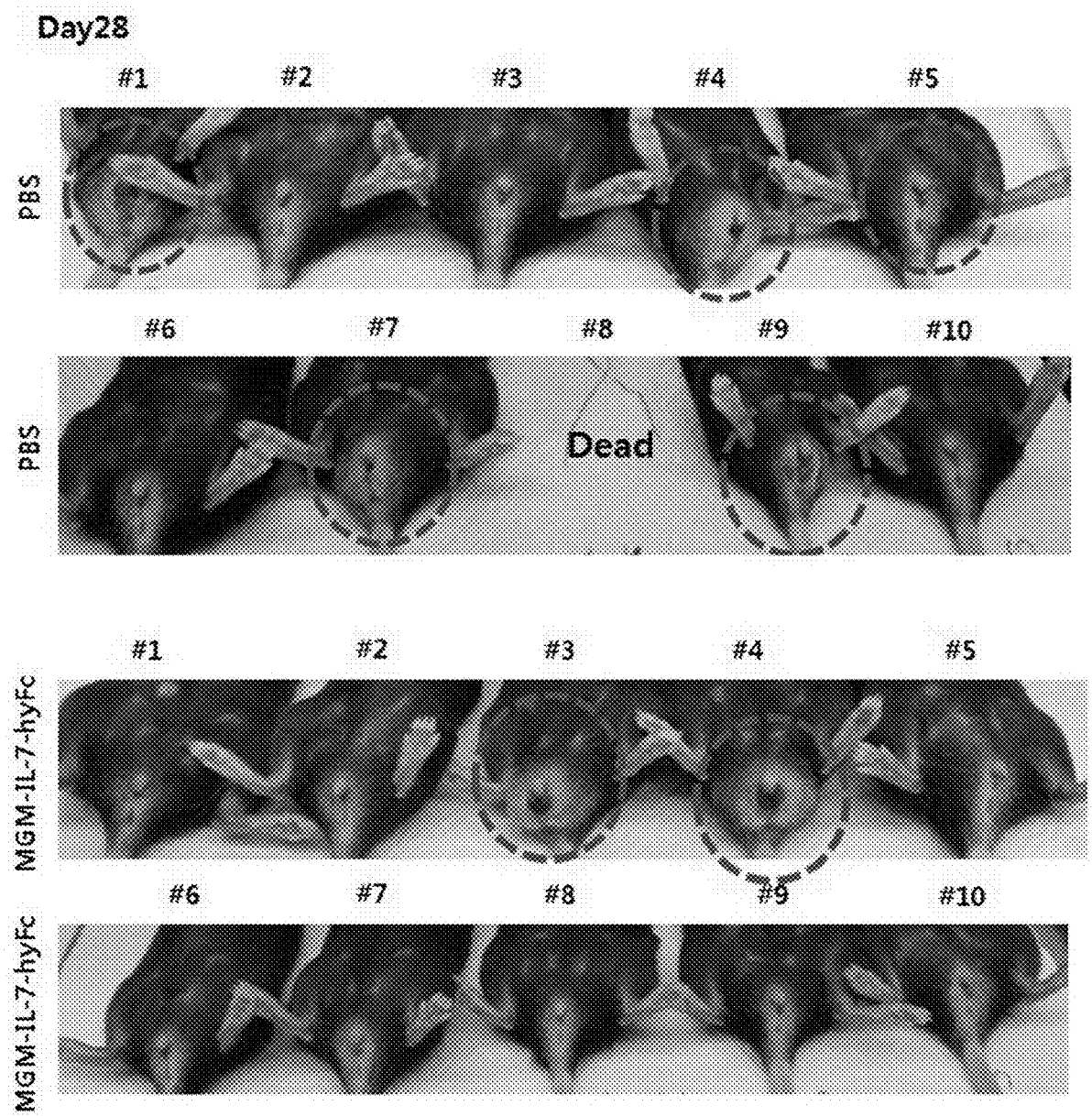
FIG. 11 shows the images of the morphological observation of anticancer effect, in a cancer cell transplant disease model, according to the administration of the prepared IL-7 fusion proteins.

As a result, 28 days after the administration of a fusion protein, the TC-1 tumor cells were engrafted to the uterine cervix or inside the vagina and grew. That is, as shown in FIG. 11, the cancer cells proliferated and exposed outside of the vaginal orifice. In the case of the control group administered with PBS, 6 out of 10 mice were observed to have the proliferation of the TC-1 cells, and one among them died due to excessive proliferation of the cancer cells.

In contrast, in the experimental group administered with the MGM-IL-7 fusion protein, only two out of 10 mice were observed to have the symptom of the proliferation of the TC-1 cells and no mice were dead. Accordingly, it was confirmed that the modified IL-7 fusion protein is effective for the prevention and treatment of cancer.

---

What is claimed is:

1. A polypeptide of the following structure:

N'-A-IL-7-C' wherein

N' and C' are the N'-terminus and the C'-terminus of the protein, respectively,

A is glycine or an oligopeptide consisting of 2 to 10 amino acid residues selected from the group consisting of methionine and glycine, and IL-7 is a protein comprising the amino acid sequence of SEQ ID NO: 1, 2, 3, 4, 5, or 6.

2. The polypeptide of claim 1, wherein the IL 7 consists of the amino acid sequence of SEQ ID NO: 1, 2, 3, 4, 5, or 6.

3. The polypeptide of claim 1, wherein A is any one selected from the group consisting of glycine, methionine-methionine, glycine-glycine, methionine-glycine, glycine-methionine, methionine-methionine-methionine, methionine-methionine-glycine, methionine-glycine-methionine, glycine-methionine-methionine, methionine-glycine-glycine, glycine-methionine-glycine, glycine-glycine-methionine, glycine-glycine-glycine, and methionine-methionine-methionine-methionine.

4. A method of preparing the polypeptide of claim 1 comprising linking glycine or an oligopeptide of 2 to 10 amino acid residues, to the N-terminal of an interleukin-7 comprising the amino acid sequence of SEQ ID NO: 1, 2, 3, 4, 5, or 6.

5. A pharmaceutical composition comprising the polypeptide according to claim 1.

6. The pharmaceutical composition of claim 5, which further comprises a pharmaceutically acceptable carrier.

7. The pharmaceutical composition of claim 6, which is an injection formulation.

8. The polypeptide of claim 1, which comprises the sequence of SEQ ID NO: 15, 16, 17, 18, 19, or 20.

9. The polypeptide of claim 1, which comprises a sequence of 95% or more identity to the sequence of SEQ ID NO: 15, 16, 17, 18, 19, or 20.

10. A pharmaceutical composition comprising the polypeptide of claim 1 and a pharmaceutically acceptable carrier.

11. A pharmaceutical composition comprising the polypeptide of claim 8 and a pharmaceutically acceptable carrier.

12. A pharmaceutical composition comprising the polypeptide of claim 9 and a pharmaceutically acceptable carrier.

* * * * *

SEQUENCE LISTING

```
<160> NUMBER OF SEQ ID NOS: 40

<210> SEQ ID NO 1
<211> LENGTH: 177
<212> TYPE: PRT
<213> ORGANISM: Homo sapiens
<220> FEATURE:
<223> OTHER INFORMATION: amino acid sequence of human IL-7 (Accession
      number: P13232)

<400> SEQUENCE: 1

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
                20                  25                  30

Asp Gly Lys Gln Tyr Glu Ser Val Leu Met Val Ser Ile Asp Gln Leu
            35                  40                  45

Leu Asp Ser Met Lys Glu Ile Gly Ser Asn Cys Leu Asn Asn Glu Phe
        50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95
```

```
Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His

<210> SEQ ID NO 2
<211> LENGTH: 154
<212> TYPE: PRT
<213> ORGANISM: Rattus norvegicus
<220> FEATURE:
<223> OTHER INFORMATION: amino acid sequence of rat IL-7 (Accession
      number: P56478)

<400> SEQUENCE: 2

Met Phe His Val Ser Phe Arg Tyr Ile Phe Gly Ile Pro Pro Leu Ile
1               5                   10                  15

Leu Val Leu Leu Pro Val Thr Ser Ser Asp Cys His Ile Lys Asp Lys
            20                  25                  30

Asp Gly Lys Ala Phe Gly Ser Val Leu Met Ile Ser Ile Asn Gln Leu
        35                  40                  45

Asp Lys Met Thr Gly Thr Asp Ser Asp Cys Pro Asn Asn Glu Pro Asn
    50                  55                  60

Phe Phe Lys Lys His Leu Cys Asp Asp Thr Lys Glu Ala Ala Phe Leu
65                  70                  75                  80

Asn Arg Ala Ala Arg Lys Leu Arg Gln Phe Leu Lys Met Asn Ile Ser
                85                  90                  95

Glu Glu Phe Asn Asp His Leu Leu Arg Val Ser Asp Gly Thr Gln Thr
            100                 105                 110

Leu Val Asn Cys Thr Ser Lys Glu Glu Lys Thr Ile Lys Glu Gln Lys
        115                 120                 125

Lys Asn Asp Pro Cys Phe Leu Lys Arg Leu Leu Arg Glu Ile Lys Thr
    130                 135                 140

Cys Trp Asn Lys Ile Leu Lys Gly Ser Ile
145                 150

<210> SEQ ID NO 3
<211> LENGTH: 154
<212> TYPE: PRT
<213> ORGANISM: Mus musculus
<220> FEATURE:
<223> OTHER INFORMATION: amino acid sequence of mouse IL-7 (Accession
      number: P10168)

<400> SEQUENCE: 3

Met Phe His Val Ser Phe Arg Tyr Ile Phe Gly Ile Pro Pro Leu Ile
1               5                   10                  15

Leu Val Leu Leu Pro Val Thr Ser Ser Glu Cys His Ile Lys Asp Lys
            20                  25                  30

Glu Gly Lys Ala Tyr Glu Ser Val Leu Met Ile Ser Ile Asp Glu Leu
        35                  40                  45

Asp Lys Met Thr Gly Thr Asp Ser Asn Cys Pro Asn Asn Glu Pro Asn
```

```
                    50                  55                  60
Phe Phe Arg Lys His Val Cys Asp Asp Thr Lys Glu Ala Ala Phe Leu
 65                  70                  75                  80

Asn Arg Ala Ala Arg Lys Leu Lys Gln Phe Leu Lys Met Asn Ile Ser
                 85                  90                  95

Glu Glu Phe Asn Val His Leu Leu Thr Val Ser Gln Gly Thr Gln Thr
                100                 105                 110

Leu Val Asn Cys Thr Ser Lys Glu Glu Lys Asn Val Lys Glu Gln Lys
            115                 120                 125

Lys Asn Asp Ala Cys Phe Leu Lys Arg Leu Leu Arg Glu Ile Lys Thr
        130                 135                 140

Cys Trp Asn Lys Ile Leu Lys Gly Ser Ile
145                 150
```

```
<210> SEQ ID NO 4
<211> LENGTH: 177
<212> TYPE: PRT
<213> ORGANISM: Chlorocebus sabaeus
<220> FEATURE:
<223> OTHER INFORMATION: amino acid sequence of monkey IL-7 (Accession
      number : NP_001279008)

<400> SEQUENCE: 4

Met Phe His Val Ser Phe Arg Tyr Ile Phe Gly Leu Pro Pro Leu Ile
 1               5                  10                  15

Leu Val Leu Leu Pro Val Ala Ser Ser Asp Cys Asp Ile Glu Gly Lys
                20                  25                  30

Asp Gly Lys Gln Tyr Glu Ser Val Leu Met Val Ser Ile Asp Gln Leu
             35                  40                  45

Leu Asp Ser Met Lys Glu Ile Gly Ser Asn Cys Leu Asn Asn Glu Phe
        50                  55                  60

Asn Phe Phe Lys Arg His Leu Cys Asp Asp Asn Lys Glu Gly Met Phe
 65                  70                  75                  80

Leu Phe Arg Ala Ala Arg Lys Leu Lys Gln Phe Leu Lys Met Asn Ser
                 85                  90                  95

Thr Gly Asp Phe Asp Leu His Leu Leu Lys Val Ser Glu Gly Thr Thr
                100                 105                 110

Ile Leu Leu Asn Cys Thr Gly Lys Val Lys Gly Arg Lys Pro Ala Ala
            115                 120                 125

Leu Gly Glu Pro Gln Pro Thr Lys Ser Leu Glu Glu Asn Lys Ser Leu
        130                 135                 140

Lys Glu Gln Lys Lys Leu Asn Asp Ser Cys Phe Leu Lys Arg Leu Leu
145                 150                 155                 160

Gln Lys Ile Lys Thr Cys Trp Asn Lys Ile Leu Met Gly Thr Lys Glu
                165                 170                 175

His
```

```
<210> SEQ ID NO 5
<211> LENGTH: 176
<212> TYPE: PRT
<213> ORGANISM: Bos taurus
<220> FEATURE:
<223> OTHER INFORMATION: amino acid sequence of cow IL-7 (Accession
      number: P26895)

<400> SEQUENCE: 5

Met Phe His Val Ser Phe Arg Tyr Ile Phe Gly Ile Pro Pro Leu Ile
 1               5                  10                  15
```

Leu Val Leu Leu Pro Val Ala Ser Ser Asp Cys Asp Ile Ser Gly Lys
            20                  25                  30

Asp Gly Gly Ala Tyr Gln Asn Val Leu Met Val Asn Ile Asp Asp Leu
        35                  40                  45

Asp Asn Met Ile Asn Phe Asp Ser Asn Cys Leu Asn Asn Glu Pro Asn
    50                  55                  60

Phe Phe Lys Lys His Ser Cys Asp Asp Asn Lys Glu Ala Ser Phe Leu
65                  70                  75                  80

Asn Arg Ala Ser Arg Lys Leu Arg Gln Phe Leu Lys Met Asn Ile Ser
                85                  90                  95

Asp Asp Phe Lys Leu His Leu Ser Thr Val Ser Gln Gly Thr Leu Thr
            100                 105                 110

Leu Leu Asn Cys Thr Ser Lys Gly Lys Gly Arg Lys Pro Pro Ser Leu
            115                 120                 125

Ser Glu Ala Gln Pro Thr Lys Asn Leu Glu Glu Asn Lys Ser Ser Lys
130                 135                 140

Glu Gln Lys Lys Gln Asn Asp Leu Cys Phe Leu Lys Ile Leu Leu Gln
145                 150                 155                 160

Lys Ile Lys Thr Cys Trp Asn Lys Ile Leu Arg Gly Ile Lys Glu His
            165                 170                 175

<210> SEQ ID NO 6
<211> LENGTH: 176
<212> TYPE: PRT
<213> ORGANISM: Ovis aries
<220> FEATURE:
<223> OTHER INFORMATION: amino acid sequence of sheep IL-7 (Accession
      number : Q28540)

<400> SEQUENCE: 6

Met Phe His Val Ser Phe Arg Tyr Ile Phe Gly Ile Pro Pro Leu Ile
1               5                   10                  15

Leu Val Leu Leu Pro Val Ala Ser Ser Asp Cys Asp Phe Ser Gly Lys
            20                  25                  30

Asp Gly Gly Ala Tyr Gln Asn Val Leu Met Val Ser Ile Asp Asp Leu
        35                  40                  45

Asp Asn Met Ile Asn Phe Asp Ser Asn Cys Leu Asn Asn Glu Pro Asn
    50                  55                  60

Phe Phe Lys Lys His Ser Cys Asp Asp Asn Lys Glu Ala Ser Phe Leu
65                  70                  75                  80

Asn Arg Ala Ala Arg Lys Leu Lys Gln Phe Leu Lys Met Asn Ile Ser
                85                  90                  95

Asp Asp Phe Lys Leu His Leu Ser Thr Val Ser Gln Gly Thr Leu Thr
            100                 105                 110

Leu Leu Asn Cys Thr Ser Lys Gly Lys Gly Arg Lys Pro Pro Ser Leu
            115                 120                 125

Gly Glu Ala Gln Pro Thr Lys Asn Leu Glu Glu Asn Lys Ser Leu Lys
        130                 135                 140

Glu Gln Arg Lys Gln Asn Asp Leu Cys Phe Leu Lys Ile Leu Leu Gln
145                 150                 155                 160

Lys Ile Lys Thr Cys Trp Asn Lys Ile Leu Arg Gly Ile Thr Glu His
            165                 170                 175

<210> SEQ ID NO 7
<211> LENGTH: 384
<212> TYPE: PRT

<213> ORGANISM: Homo sapiens
<220> FEATURE:
<223> OTHER INFORMATION: amino acid sequence of human IgD constant
region (Genbank accession No. P01880)

<400> SEQUENCE: 7

```
Ala Pro Thr Lys Ala Pro Asp Val Phe Pro Ile Ile Ser Gly Cys Arg
  1               5                  10                  15

His Pro Lys Asp Asn Ser Pro Val Val Leu Ala Cys Leu Ile Thr Gly
             20                  25                  30

Tyr His Pro Thr Ser Val Thr Val Thr Trp Tyr Met Gly Thr Gln Ser
         35                  40                  45

Gln Pro Gln Arg Thr Phe Pro Glu Ile Gln Arg Arg Asp Ser Tyr Tyr
     50                  55                  60

Met Thr Ser Ser Gln Leu Ser Thr Pro Leu Gln Gln Trp Arg Gln Gly
 65                  70                  75                  80

Glu Tyr Lys Cys Val Val Gln His Thr Ala Ser Lys Ser Lys Lys Glu
             85                  90                  95

Ile Phe Arg Trp Pro Glu Ser Pro Lys Ala Gln Ala Ser Ser Val Pro
        100                 105                 110

Thr Ala Gln Pro Gln Ala Glu Gly Ser Leu Ala Lys Ala Thr Thr Ala
        115                 120                 125

Pro Ala Thr Thr Arg Asn Thr Gly Arg Gly Gly Glu Glu Lys Lys Lys
130                 135                 140

Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala
                165                 170                 175

Val Gln Asp Leu Trp Leu Arg Asp Lys Ala Thr Phe Thr Cys Phe Val
            180                 185                 190

Val Gly Ser Asp Leu Lys Asp Ala His Leu Thr Trp Glu Val Ala Gly
            195                 200                 205

Lys Val Pro Thr Gly Gly Val Glu Glu Gly Leu Leu Glu Arg His Ser
210                 215                 220

Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
                245                 250                 255

Pro Pro Gln Arg Leu Met Ala Leu Arg Glu Pro Ala Ala Gln Ala Pro
            260                 265                 270

Val Lys Leu Ser Leu Asn Leu Leu Ala Ser Ser Asp Pro Pro Glu Ala
            275                 280                 285

Ala Ser Trp Leu Leu Cys Glu Val Ser Gly Phe Ser Pro Pro Asn Ile
        290                 295                 300

Leu Leu Met Trp Leu Glu Asp Gln Arg Glu Val Asn Thr Ser Gly Phe
305                 310                 315                 320

Ala Pro Ala Arg Pro Pro Gln Pro Gly Ser Thr Thr Phe Trp Ala
                325                 330                 335

Trp Ser Val Leu Arg Val Pro Ala Pro Pro Ser Pro Gln Pro Ala Thr
            340                 345                 350

Tyr Thr Cys Val Val Ser His Glu Asp Ser Arg Thr Leu Leu Asn Ala
        355                 360                 365

Ser Arg Ser Leu Glu Val Ser Tyr Val Thr Asp His Gly Pro Met Lys
370                 375                 380
```

<210> SEQ ID NO 8
<211> LENGTH: 327
<212> TYPE: PRT
<213> ORGANISM: Homo sapiens
<220> FEATURE:
<223> OTHER INFORMATION: amino acid sequence of Partial human IgG4
      constant region (Genbank accession No. AAH25985)

<400> SEQUENCE: 8

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 9
<211> LENGTH: 245
<212> TYPE: PRT
<213> ORGANISM: Artificial Sequence
<220> FEATURE:
<223> OTHER INFORMATION: amino acid sequence of hyFc

<400> SEQUENCE: 9

Arg Asn Thr Gly Arg Gly Gly Glu Glu Lys Lys Lys Glu Lys Glu Lys
1               5                   10                  15

Glu Glu Gln Glu Glu Arg Glu Thr Lys Thr Pro Glu Cys Pro Ser His
                20                  25                  30

Thr Gln Pro Leu Gly Val Phe Leu Phe Pro Pro Lys Pro Lys Asp Thr
            35                  40                  45

Leu Met Ile Ser Arg Thr Pro Glu Val Thr Cys Val Val Val Asp Val
    50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Gly Leu Pro Ser
        115                 120                 125

Ser Ile Glu Lys Thr Ile Ser Lys Ala Lys Gly Gln Pro Arg Glu Pro
    130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
        195                 200                 205

Thr Val Asp Lys Ser Arg Trp Gln Gln Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Leu Gly Lys
                245

<210> SEQ ID NO 10
<211> LENGTH: 245
<212> TYPE: PRT
<213> ORGANISM: Artificial Sequence
<220> FEATURE:
<223> OTHER INFORMATION: amino acid sequence of hyFcM1

<400> SEQUENCE: 10

Arg Asn Thr Gly Arg Gly Gly Glu Glu Lys Lys Gly Gly Lys Glu Lys
1               5                   10                  15

Glu Glu Gln Glu Glu Arg Glu Thr Lys Thr Pro Glu Cys Pro Ser His
                20                  25                  30

Thr Gln Pro Leu Gly Val Phe Leu Phe Pro Pro Lys Pro Lys Asp Thr
            35                  40                  45

Leu Met Ile Ser Arg Thr Pro Glu Val Thr Cys Val Val Val Asp Val
    50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser

```
                        85                  90                  95

Thr Tyr Arg Val Val Ser Val Leu Thr Val Leu His Gln Asp Trp Leu
                100                 105                 110

Asn Gly Lys Glu Tyr Lys Cys Lys Val Ser Asn Lys Gly Leu Pro Ser
            115                 120                 125

Ser Ile Glu Lys Thr Ile Ser Lys Ala Lys Gly Gln Pro Arg Glu Pro
        130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
        195                 200                 205

Thr Val Asp Lys Ser Arg Trp Gln Glu Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Leu Gly Lys
                245

<210> SEQ ID NO 11
<211> LENGTH: 245
<212> TYPE: PRT
<213> ORGANISM: Artificial Sequence
<220> FEATURE:
<223> OTHER INFORMATION: amino acid sequence of hyFcM2

<400> SEQUENCE: 11

Arg Asn Thr Gly Arg Gly Gly Glu Glu Lys Lys Gly Ser Lys Glu Lys
1               5                   10                  15

Glu Glu Gln Glu Glu Arg Glu Thr Lys Thr Pro Glu Cys Pro Ser His
            20                  25                  30

Thr Gln Pro Leu Gly Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Tyr Arg Val Val Ser Val Leu Thr Val Leu His Gln Asp Trp Leu
                100                 105                 110

Asn Gly Lys Glu Tyr Lys Cys Lys Val Ser Asn Lys Gly Leu Pro Ser
            115                 120                 125

Ser Ile Glu Lys Thr Ile Ser Lys Ala Lys Gly Gln Pro Arg Glu Pro
        130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
```

```
                195                 200                 205
Thr Val Asp Lys Ser Arg Trp Gln Glu Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Leu Gly Lys
                245

<210> SEQ ID NO 12
<211> LENGTH: 245
<212> TYPE: PRT
<213> ORGANISM: Artificial Sequence
<220> FEATURE:
<223> OTHER INFORMATION: amino acid sequence of hyFcM3

<400> SEQUENCE: 12

Arg Asn Thr Gly Arg Gly Gly Glu Glu Lys Lys Ser Gly Lys Glu Lys
1               5                   10                  15

Glu Glu Gln Glu Glu Arg Glu Thr Lys Thr Pro Glu Cys Pro Ser His
                20                  25                  30

Thr Gln Pro Leu Gly Val Phe Leu Phe Pro Pro Lys Pro Lys Asp Thr
            35                  40                  45

Leu Met Ile Ser Arg Thr Pro Glu Val Thr Cys Val Val Val Asp Val
    50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Gly Leu Pro Ser
        115                 120                 125

Ser Ile Glu Lys Thr Ile Ser Lys Ala Lys Gly Gln Pro Arg Glu Pro
    130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
        195                 200                 205

Thr Val Asp Lys Ser Arg Trp Gln Glu Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Leu Gly Lys
                245

<210> SEQ ID NO 13
<211> LENGTH: 245
<212> TYPE: PRT
<213> ORGANISM: Artificial Sequence
<220> FEATURE:
<223> OTHER INFORMATION: amino acid sequence of hyFcM4

<400> SEQUENCE: 13
```

Arg Asn Thr Gly Arg Gly Gly Glu Glu Lys Ser Lys Glu Lys
1               5                   10                  15

Glu Glu Gln Glu Glu Arg Glu Thr Lys Thr Pro Glu Cys Pro Ser His
            20                  25                  30

Thr Gln Pro Leu Gly Val Phe Leu Phe Pro Pro Lys Pro Lys Asp Thr
            35                  40                  45

Leu Met Ile Ser Arg Thr Pro Glu Val Thr Cys Val Val Asp Val
    50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Gly Leu Pro Ser
            115                 120                 125

Ser Ile Glu Lys Thr Ile Ser Lys Ala Lys Gly Gln Pro Arg Glu Pro
    130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
            165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
    195                 200                 205

Thr Val Asp Lys Ser Arg Trp Gln Glu Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Leu Gly Lys
                245

<210> SEQ ID NO 14
<211> LENGTH: 243
<212> TYPE: PRT
<213> ORGANISM: Artificial Sequence
<220> FEATURE:
<223> OTHER INFORMATION: amino acid sequence of mouse IgG Fc variant

<400> SEQUENCE: 14

Ala Ser Ala Glu Pro Arg Gly Pro Thr Ile Lys Pro Cys Pro Pro Cys
1               5                   10                  15

Lys Cys Pro Ala Pro Asn Leu Glu Gly Gly Pro Ser Val Phe Ile Phe
            20                  25                  30

Pro Pro Lys Ile Lys Asp Val Leu Met Ile Ser Leu Ser Pro Ile Val
            35                  40                  45

Thr Cys Val Val Val Asp Val Ser Glu Asp Asp Pro Asp Val Gln Ile
        50                  55                  60

Ser Trp Phe Val Asn Asn Val Glu Val His Thr Ala Gln Thr Gln Thr
65                  70                  75                  80

His Arg Glu Asp Tyr Asn Ser Thr Leu Arg Val Val Ser Ala Leu Pro
                85                  90                  95

Ile Gln His Gln Asp Trp Met Ser Gly Lys Ala Phe Ala Cys Ala Val
            100                 105                 110

```
Asn Asn Lys Asp Leu Pro Ala Pro Ile Glu Arg Thr Ile Ser Lys Pro
            115                 120                 125

Lys Gly Ser Val Arg Ala Pro Gln Val Tyr Val Leu Pro Pro Pro Glu
        130                 135                 140

Glu Glu Met Thr Lys Lys Gln Val Thr Leu Thr Cys Met Val Thr Asp
145                 150                 155                 160

Phe Met Pro Glu Asp Ile Tyr Val Glu Trp Thr Asn Asn Gly Lys Thr
                165                 170                 175

Glu Leu Asn Tyr Lys Asn Thr Glu Pro Val Leu Asp Ser Asp Gly Ser
            180                 185                 190

Tyr Phe Met Tyr Ser Lys Leu Arg Val Glu Lys Lys Asn Trp Val Glu
        195                 200                 205

Arg Asn Ser Tyr Ser Cys Ser Val Val His Glu Gly Leu His Asn His
    210                 215                 220

His Thr Thr Lys Ser Phe Ser Arg Thr Pro Gly Lys Gly Gly Gly Asn
225                 230                 235                 240

Ser Gly Ser

<210> SEQ ID NO 15
<211> LENGTH: 153
<212> TYPE: PRT
<213> ORGANISM: Artificial Sequence
<220> FEATURE:
<223> OTHER INFORMATION: amino acid sequence of modified IL-7(M)

<400> SEQUENCE: 15

Met Asp Cys Asp Ile Glu Gly Lys Asp Gly Lys Gln Tyr Glu Ser Val
1               5                   10                  15

Leu Met Val Ser Ile Asp Gln Leu Leu Asp Ser Met Lys Glu Ile Gly
            20                  25                  30

Ser Asn Cys Leu Asn Asn Glu Phe Asn Phe Phe Lys Arg His Ile Cys
        35                  40                  45

Asp Ala Asn Lys Glu Gly Met Phe Leu Phe Arg Ala Ala Arg Lys Leu
    50                  55                  60

Arg Gln Phe Leu Lys Met Asn Ser Thr Gly Asp Phe Asp Leu His Leu
65                  70                  75                  80

Leu Lys Val Ser Glu Gly Thr Thr Ile Leu Leu Asn Cys Thr Gly Gln
                85                  90                  95

Val Lys Gly Arg Lys Pro Ala Ala Leu Gly Glu Ala Gln Pro Thr Lys
            100                 105                 110

Ser Leu Glu Glu Asn Lys Ser Leu Lys Glu Gln Lys Lys Leu Asn Asp
        115                 120                 125

Leu Cys Phe Leu Lys Arg Leu Leu Gln Glu Ile Lys Thr Cys Trp Asn
    130                 135                 140

Lys Ile Leu Met Gly Thr Lys Glu His
145                 150

<210> SEQ ID NO 16
<211> LENGTH: 154
<212> TYPE: PRT
<213> ORGANISM: Artificial Sequence
<220> FEATURE:
<223> OTHER INFORMATION: amino acid sequence of modified IL-7(MM)

<400> SEQUENCE: 16

Met Met Asp Cys Asp Ile Glu Gly Lys Asp Gly Lys Gln Tyr Glu Ser
1               5                   10                  15
```

```
Val Leu Met Val Ser Ile Asp Gln Leu Leu Asp Ser Met Lys Glu Ile
            20                  25                  30

Gly Ser Asn Cys Leu Asn Asn Glu Phe Asn Phe Phe Lys Arg His Ile
            35                  40                  45

Cys Asp Ala Asn Lys Glu Gly Met Phe Leu Phe Arg Ala Ala Arg Lys
            50                  55                  60

Leu Arg Gln Phe Leu Lys Met Asn Ser Thr Gly Asp Phe Asp Leu His
65                  70                  75                  80

Leu Leu Lys Val Ser Glu Gly Thr Thr Ile Leu Leu Asn Cys Thr Gly
                85                  90                  95

Gln Val Lys Gly Arg Lys Pro Ala Ala Leu Gly Glu Ala Gln Pro Thr
                100                 105                 110

Lys Ser Leu Glu Glu Asn Lys Ser Leu Lys Glu Gln Lys Lys Leu Asn
            115                 120                 125

Asp Leu Cys Phe Leu Lys Arg Leu Leu Gln Glu Ile Lys Thr Cys Trp
            130                 135                 140

Asn Lys Ile Leu Met Gly Thr Lys Glu His
145                 150

<210> SEQ ID NO 17
<211> LENGTH: 155
<212> TYPE: PRT
<213> ORGANISM: Artificial Sequence
<220> FEATURE:
<223> OTHER INFORMATION: amino acid sequence of modified IL-7(MMM)

<400> SEQUENCE: 17

Met Met Met Asp Cys Asp Ile Glu Gly Lys Asp Gly Lys Gln Tyr Glu
1               5                   10                  15

Ser Val Leu Met Val Ser Ile Asp Gln Leu Leu Asp Ser Met Lys Glu
            20                  25                  30

Ile Gly Ser Asn Cys Leu Asn Asn Glu Phe Asn Phe Phe Lys Arg His
            35                  40                  45

Ile Cys Asp Ala Asn Lys Glu Gly Met Phe Leu Phe Arg Ala Ala Arg
            50                  55                  60

Lys Leu Arg Gln Phe Leu Lys Met Asn Ser Thr Gly Asp Phe Asp Leu
65                  70                  75                  80

His Leu Leu Lys Val Ser Glu Gly Thr Thr Ile Leu Leu Asn Cys Thr
                85                  90                  95

Gly Gln Val Lys Gly Arg Lys Pro Ala Ala Leu Gly Glu Ala Gln Pro
                100                 105                 110

Thr Lys Ser Leu Glu Glu Asn Lys Ser Leu Lys Glu Gln Lys Lys Leu
            115                 120                 125

Asn Asp Leu Cys Phe Leu Lys Arg Leu Leu Gln Glu Ile Lys Thr Cys
            130                 135                 140

Trp Asn Lys Ile Leu Met Gly Thr Lys Glu His
145                 150                 155

<210> SEQ ID NO 18
<211> LENGTH: 155
<212> TYPE: PRT
<213> ORGANISM: Artificial Sequence
<220> FEATURE:
<223> OTHER INFORMATION: amino acid sequence of modified IL-7(MGM)

<400> SEQUENCE: 18

Met Gly Met Asp Cys Asp Ile Glu Gly Lys Asp Gly Lys Gln Tyr Glu
1               5                   10                  15
```

Ser Val Leu Met Val Ser Ile Asp Gln Leu Leu Asp Ser Met Lys Glu
            20                  25                  30

Ile Gly Ser Asn Cys Leu Asn Asn Glu Phe Asn Phe Phe Lys Arg His
        35                  40                  45

Ile Cys Asp Ala Asn Lys Glu Gly Met Phe Leu Phe Arg Ala Ala Arg
    50                  55                  60

Lys Leu Arg Gln Phe Leu Lys Met Asn Ser Thr Gly Asp Phe Asp Leu
65                  70                  75                  80

His Leu Leu Lys Val Ser Glu Gly Thr Thr Ile Leu Leu Asn Cys Thr
                85                  90                  95

Gly Gln Val Lys Gly Arg Lys Pro Ala Ala Leu Gly Glu Ala Gln Pro
            100                 105                 110

Thr Lys Ser Leu Glu Glu Asn Lys Ser Leu Lys Glu Gln Lys Lys Leu
        115                 120                 125

Asn Asp Leu Cys Phe Leu Lys Arg Leu Leu Gln Glu Ile Lys Thr Cys
    130                 135                 140

Trp Asn Lys Ile Leu Met Gly Thr Lys Glu His
145                 150                 155

<210> SEQ ID NO 19
<211> LENGTH: 155
<212> TYPE: PRT
<213> ORGANISM: Artificial Sequence
<220> FEATURE:
<223> OTHER INFORMATION: amino acid sequence of modified IL-7(DDD)

<400> SEQUENCE: 19

Asp Asp Asp Asp Cys Asp Ile Glu Gly Lys Asp Gly Lys Gln Tyr Glu
1               5                   10                  15

Ser Val Leu Met Val Ser Ile Asp Gln Leu Leu Asp Ser Met Lys Glu
            20                  25                  30

Ile Gly Ser Asn Cys Leu Asn Asn Glu Phe Asn Phe Phe Lys Arg His
        35                  40                  45

Ile Cys Asp Ala Asn Lys Glu Gly Met Phe Leu Phe Arg Ala Ala Arg
    50                  55                  60

Lys Leu Arg Gln Phe Leu Lys Met Asn Ser Thr Gly Asp Phe Asp Leu
65                  70                  75                  80

His Leu Leu Lys Val Ser Glu Gly Thr Thr Ile Leu Leu Asn Cys Thr
                85                  90                  95

Gly Gln Val Lys Gly Arg Lys Pro Ala Ala Leu Gly Glu Ala Gln Pro
            100                 105                 110

Thr Lys Ser Leu Glu Glu Asn Lys Ser Leu Lys Glu Gln Lys Lys Leu
        115                 120                 125

Asn Asp Leu Cys Phe Leu Lys Arg Leu Leu Gln Glu Ile Lys Thr Cys
    130                 135                 140

Trp Asn Lys Ile Leu Met Gly Thr Lys Glu His
145                 150                 155

<210> SEQ ID NO 20
<211> LENGTH: 156
<212> TYPE: PRT
<213> ORGANISM: Artificial Sequence
<220> FEATURE:
<223> OTHER INFORMATION: amino acid sequence of modified IL-7(MMMM)

<400> SEQUENCE: 20

Met Met Met Met Asp Cys Asp Ile Glu Gly Lys Asp Gly Lys Gln Tyr

```
                1               5                    10                   15
            Glu Ser Val Leu Met Val Ser Ile Asp Gln Leu Leu Asp Ser Met Lys
                               20                   25                   30

Glu Ile Gly Ser Asn Cys Leu Asn Asn Glu Phe Asn Phe Phe Lys Arg
                               35                   40                   45

His Ile Cys Asp Ala Asn Lys Glu Gly Met Phe Leu Phe Arg Ala Ala
                50                            55                       60

Arg Lys Leu Arg Gln Phe Leu Lys Met Asn Ser Thr Gly Asp Phe Asp
            65                       70                   75                   80

Leu His Leu Leu Lys Val Ser Glu Gly Thr Thr Ile Leu Leu Asn Cys
                               85                   90                   95

Thr Gly Gln Val Lys Gly Arg Lys Pro Ala Ala Leu Gly Glu Ala Gln
                              100                  105                  110

Pro Thr Lys Ser Leu Glu Glu Asn Lys Ser Leu Lys Glu Gln Lys Lys
                              115                  120                  125

Leu Asn Asp Leu Cys Phe Leu Lys Arg Leu Leu Gln Glu Ile Lys Thr
                              130                  135                  140

Cys Trp Asn Lys Ile Leu Met Gly Thr Lys Glu His
            145                      150                  155
```

<210> SEQ ID NO 21
<211> LENGTH: 398
<212> TYPE: PRT
<213> ORGANISM: Artificial Sequence
<220> FEATURE:
<223> OTHER INFORMATION: amino acid sequence of modified IL-7(M) fused hyFc

<400> SEQUENCE: 21

```
            Met Asp Cys Asp Ile Glu Gly Lys Asp Gly Lys Gln Tyr Glu Ser Val
            1                 5                   10                   15

Leu Met Val Ser Ile Asp Gln Leu Leu Asp Ser Met Lys Glu Ile Gly
                             20                   25                   30

Ser Asn Cys Leu Asn Asn Glu Phe Asn Phe Phe Lys Arg His Ile Cys
                             35                   40                   45

Asp Ala Asn Lys Glu Gly Met Phe Leu Phe Arg Ala Ala Arg Lys Leu
                50                            55                       60

Arg Gln Phe Leu Lys Met Asn Ser Thr Gly Asp Phe Asp Leu His Leu
            65                       70                   75                   80

Leu Lys Val Ser Glu Gly Thr Thr Ile Leu Leu Asn Cys Thr Gly Gln
                             85                   90                   95

Val Lys Gly Arg Lys Pro Ala Ala Leu Gly Glu Ala Gln Pro Thr Lys
                            100                  105                  110

Ser Leu Glu Glu Asn Lys Ser Leu Lys Glu Gln Lys Lys Leu Asn Asp
                            115                  120                  125

Leu Cys Phe Leu Lys Arg Leu Leu Gln Glu Ile Lys Thr Cys Trp Asn
                            130                  135                  140

Lys Ile Leu Met Gly Thr Lys Glu His Arg Asn Thr Gly Arg Gly Gly
            145                      150                  155                  160

Glu Glu Lys Lys Lys Glu Lys Glu Lys Glu Glu Gln Glu Glu Arg Glu
                            165                  170                  175

Thr Lys Thr Pro Glu Cys Pro Ser His Thr Gln Pro Leu Gly Val Phe
                            180                  185                  190

Leu Phe Pro Pro Lys Pro Lys Asp Thr Leu Met Ile Ser Arg Thr Pro
                            195                  200                  205
```

```
Glu Val Thr Cys Val Val Val Asp Val Ser Gln Glu Asp Pro Glu Val
            210                 215                 220
Gln Phe Asn Trp Tyr Val Asp Gly Val Glu Val His Asn Ala Lys Thr
225                 230                 235                 240
Lys Pro Arg Glu Glu Gln Phe Asn Ser Thr Tyr Arg Val Val Ser Val
                245                 250                 255
Leu Thr Val Leu His Gln Asp Trp Leu Asn Gly Lys Glu Tyr Lys Cys
            260                 265                 270
Lys Val Ser Asn Lys Gly Leu Pro Ser Ser Ile Glu Lys Thr Ile Ser
        275                 280                 285
Lys Ala Lys Gly Gln Pro Arg Glu Pro Gln Val Tyr Thr Leu Pro Pro
290                 295                 300
Ser Gln Glu Glu Met Thr Lys Asn Gln Val Ser Leu Thr Cys Leu Val
305                 310                 315                 320
Lys Gly Phe Tyr Pro Ser Asp Ile Ala Val Glu Trp Glu Ser Asn Gly
                325                 330                 335
Gln Pro Glu Asn Asn Tyr Lys Thr Thr Pro Pro Val Leu Asp Ser Asp
            340                 345                 350
Gly Ser Phe Phe Leu Tyr Ser Arg Leu Thr Val Asp Lys Ser Arg Trp
        355                 360                 365
Gln Glu Gly Asn Val Phe Ser Cys Ser Val Met His Glu Ala Leu His
370                 375                 380
Asn His Tyr Thr Gln Lys Ser Leu Ser Leu Ser Leu Gly Lys
385                 390                 395

<210> SEQ ID NO 22
<211> LENGTH: 399
<212> TYPE: PRT
<213> ORGANISM: Artificial Sequence
<220> FEATURE:
<223> OTHER INFORMATION: amino acid sequence of modified IL-7(MM) fused
      hyFc

<400> SEQUENCE: 22

Met Met Asp Cys Asp Ile Glu Gly Lys Asp Gly Lys Gln Tyr Glu Ser
1               5                   10                  15
Val Leu Met Val Ser Ile Asp Gln Leu Leu Asp Ser Met Lys Glu Ile
                20                  25                  30
Gly Ser Asn Cys Leu Asn Asn Glu Phe Asn Phe Phe Lys Arg His Ile
            35                  40                  45
Cys Asp Ala Asn Lys Glu Gly Met Phe Leu Phe Arg Ala Ala Arg Lys
        50                  55                  60
Leu Arg Gln Phe Leu Lys Met Asn Ser Thr Gly Asp Phe Asp Leu His
65                  70                  75                  80
Leu Leu Lys Val Ser Glu Gly Thr Thr Ile Leu Leu Asn Cys Thr Gly
                85                  90                  95
Gln Val Lys Gly Arg Lys Pro Ala Ala Leu Gly Glu Ala Gln Pro Thr
                100                 105                 110
Lys Ser Leu Glu Glu Asn Lys Ser Leu Lys Glu Gln Lys Lys Leu Asn
            115                 120                 125
Asp Leu Cys Phe Leu Lys Arg Leu Leu Gln Glu Ile Lys Thr Cys Trp
        130                 135                 140
Asn Lys Ile Leu Met Gly Thr Lys Glu His Arg Asn Thr Gly Arg Gly
145                 150                 155                 160
Gly Glu Glu Lys Lys Lys Glu Lys Glu Lys Glu Gln Glu Glu Arg
                165                 170                 175
```

```
Glu Thr Lys Thr Pro Glu Cys Pro Ser His Thr Gln Pro Leu Gly Val
            180                 185                 190

Phe Leu Phe Pro Pro Lys Pro Lys Asp Thr Leu Met Ile Ser Arg Thr
        195                 200                 205

Pro Glu Val Thr Cys Val Val Val Asp Val Ser Gln Glu Asp Pro Glu
    210                 215                 220

Val Gln Phe Asn Trp Tyr Val Asp Gly Val Glu Val His Asn Ala Lys
225                 230                 235                 240

Thr Lys Pro Arg Glu Glu Gln Phe Asn Ser Thr Tyr Arg Val Val Ser
                245                 250                 255

Val Leu Thr Val Leu His Gln Asp Trp Leu Asn Gly Lys Glu Tyr Lys
            260                 265                 270

Cys Lys Val Ser Asn Lys Gly Leu Pro Ser Ser Ile Glu Lys Thr Ile
        275                 280                 285

Ser Lys Ala Lys Gly Gln Pro Arg Glu Pro Gln Val Tyr Thr Leu Pro
    290                 295                 300

Pro Ser Gln Glu Glu Met Thr Lys Asn Gln Val Ser Leu Thr Cys Leu
305                 310                 315                 320

Val Lys Gly Phe Tyr Pro Ser Asp Ile Ala Val Glu Trp Glu Ser Asn
                325                 330                 335

Gly Gln Pro Glu Asn Asn Tyr Lys Thr Thr Pro Pro Val Leu Asp Ser
            340                 345                 350

Asp Gly Ser Phe Phe Leu Tyr Ser Arg Leu Thr Val Asp Lys Ser Arg
        355                 360                 365

Trp Gln Glu Gly Asn Val Phe Ser Cys Ser Val Met His Glu Ala Leu
    370                 375                 380

His Asn His Tyr Thr Gln Lys Ser Leu Ser Leu Ser Leu Gly Lys
385                 390                 395

<210> SEQ ID NO 23
<211> LENGTH: 400
<212> TYPE: PRT
<213> ORGANISM: Artificial Sequence
<220> FEATURE:
<223> OTHER INFORMATION: amino acid sequence of modified IL-7(MMM) fused
      hyFc

<400> SEQUENCE: 23

Met Met Met Asp Cys Asp Ile Glu Gly Lys Asp Gly Lys Gln Tyr Glu
1               5                   10                  15

Ser Val Leu Met Val Ser Ile Asp Gln Leu Leu Asp Ser Met Lys Glu
            20                  25                  30

Ile Gly Ser Asn Cys Leu Asn Asn Glu Phe Asn Phe Phe Lys Arg His
        35                  40                  45

Ile Cys Asp Ala Asn Lys Glu Gly Met Phe Leu Phe Arg Ala Ala Arg
    50                  55                  60

Lys Leu Arg Gln Phe Leu Lys Met Asn Ser Thr Gly Asp Phe Asp Leu
65                  70                  75                  80

His Leu Leu Lys Val Ser Glu Gly Thr Thr Ile Leu Leu Asn Cys Thr
                85                  90                  95

Gly Gln Val Lys Gly Arg Lys Pro Ala Ala Leu Gly Glu Ala Gln Pro
            100                 105                 110

Thr Lys Ser Leu Glu Glu Asn Lys Ser Leu Lys Glu Gln Lys Lys Leu
        115                 120                 125

Asn Asp Leu Cys Phe Leu Lys Arg Leu Leu Gln Glu Ile Lys Thr Cys
```

```
                130             135             140
Trp Asn Lys Ile Leu Met Gly Thr Lys Glu His Arg Asn Thr Gly Arg
145                 150                 155                 160

Gly Gly Glu Glu Lys Lys Glu Lys Glu Lys Glu Gln Glu Glu
                165                 170                 175

Arg Glu Thr Lys Thr Pro Glu Cys Pro Ser His Thr Gln Pro Leu Gly
                180                 185                 190

Val Phe Leu Phe Pro Pro Lys Pro Lys Asp Thr Leu Met Ile Ser Arg
                195                 200                 205

Thr Pro Glu Val Thr Cys Val Val Val Asp Val Ser Gln Glu Asp Pro
210                 215                 220

Glu Val Gln Phe Asn Trp Tyr Val Asp Gly Val Glu Val His Asn Ala
225                 230                 235                 240

Lys Thr Lys Pro Arg Glu Glu Gln Phe Asn Ser Thr Tyr Arg Val Val
                245                 250                 255

Ser Val Leu Thr Val Leu His Gln Asp Trp Leu Asn Gly Lys Glu Tyr
                260                 265                 270

Lys Cys Lys Val Ser Asn Lys Gly Leu Pro Ser Ser Ile Glu Lys Thr
275                 280                 285

Ile Ser Lys Ala Lys Gly Gln Pro Arg Glu Pro Gln Val Tyr Thr Leu
290                 295                 300

Pro Pro Ser Gln Glu Glu Met Thr Lys Asn Gln Val Ser Leu Thr Cys
305                 310                 315                 320

Leu Val Lys Gly Phe Tyr Pro Ser Asp Ile Ala Val Glu Trp Glu Ser
                325                 330                 335

Asn Gly Gln Pro Glu Asn Asn Tyr Lys Thr Thr Pro Pro Val Leu Asp
                340                 345                 350

Ser Asp Gly Ser Phe Phe Leu Tyr Ser Arg Leu Thr Val Asp Lys Ser
                355                 360                 365

Arg Trp Gln Glu Gly Asn Val Phe Ser Cys Ser Val Met His Glu Ala
370                 375                 380

Leu His Asn His Tyr Thr Gln Lys Ser Leu Ser Leu Ser Leu Gly Lys
385                 390                 395                 400

<210> SEQ ID NO 24
<211> LENGTH: 400
<212> TYPE: PRT
<213> ORGANISM: Artificial Sequence
<220> FEATURE:
<223> OTHER INFORMATION: amino acid sequence of modified IL-7(MGM) fused
      hyFc

<400> SEQUENCE: 24

Met Gly Met Asp Cys Asp Ile Glu Gly Lys Asp Gly Lys Gln Tyr Glu
1               5                   10                  15

Ser Val Leu Met Val Ser Ile Asp Gln Leu Leu Asp Ser Met Lys Glu
                20                  25                  30

Ile Gly Ser Asn Cys Leu Asn Asn Glu Phe Asn Phe Lys Arg His
                35                  40                  45

Ile Cys Asp Ala Asn Lys Glu Gly Met Phe Leu Phe Arg Ala Ala Arg
50                  55                  60

Lys Leu Arg Gln Phe Leu Lys Met Asn Ser Thr Gly Asp Phe Asp Leu
65                  70                  75                  80

His Leu Leu Lys Val Ser Glu Gly Thr Thr Ile Leu Leu Asn Cys Thr
                85                  90                  95
```

```
Gly Gln Val Lys Gly Arg Lys Pro Ala Ala Leu Gly Glu Ala Gln Pro
                100                 105                 110

Thr Lys Ser Leu Glu Glu Asn Lys Ser Leu Lys Glu Gln Lys Lys Leu
            115                 120                 125

Asn Asp Leu Cys Phe Leu Lys Arg Leu Leu Gln Glu Ile Lys Thr Cys
        130                 135                 140

Trp Asn Lys Ile Leu Met Gly Thr Lys Glu His Arg Asn Thr Gly Arg
145                 150                 155                 160

Gly Gly Glu Glu Lys Lys Glu Lys Lys Glu Glu Gln Glu Glu
                165                 170                 175

Arg Glu Thr Lys Thr Pro Glu Cys Pro Ser His Thr Gln Pro Leu Gly
                180                 185                 190

Val Phe Leu Phe Pro Pro Lys Pro Lys Asp Thr Leu Met Ile Ser Arg
            195                 200                 205

Thr Pro Glu Val Thr Cys Val Val Val Asp Val Ser Gln Glu Asp Pro
        210                 215                 220

Glu Val Gln Phe Asn Trp Tyr Val Asp Gly Val Glu Val His Asn Ala
225                 230                 235                 240

Lys Thr Lys Pro Arg Glu Glu Gln Phe Asn Ser Thr Tyr Arg Val Val
                245                 250                 255

Ser Val Leu Thr Val Leu His Gln Asp Trp Leu Asn Gly Lys Glu Tyr
            260                 265                 270

Lys Cys Lys Val Ser Asn Lys Gly Leu Pro Ser Ser Ile Glu Lys Thr
        275                 280                 285

Ile Ser Lys Ala Lys Gly Gln Pro Arg Glu Pro Gln Val Tyr Thr Leu
290                 295                 300

Pro Pro Ser Gln Glu Glu Met Thr Lys Asn Gln Val Ser Leu Thr Cys
305                 310                 315                 320

Leu Val Lys Gly Phe Tyr Pro Ser Asp Ile Ala Val Glu Trp Glu Ser
                325                 330                 335

Asn Gly Gln Pro Glu Asn Asn Tyr Lys Thr Thr Pro Pro Val Leu Asp
            340                 345                 350

Ser Asp Gly Ser Phe Phe Leu Tyr Ser Arg Leu Thr Val Asp Lys Ser
        355                 360                 365

Arg Trp Gln Glu Gly Asn Val Phe Ser Cys Ser Val Met His Glu Ala
    370                 375                 380

Leu His Asn His Tyr Thr Gln Lys Ser Leu Ser Leu Ser Leu Gly Lys
385                 390                 395                 400

<210> SEQ ID NO 25
<211> LENGTH: 401
<212> TYPE: PRT
<213> ORGANISM: Artificial Sequence
<220> FEATURE:
<223> OTHER INFORMATION: amino acid sequence of modified IL-7(MMMM)
      fused hyFc

<400> SEQUENCE: 25

Met Met Met Met Asp Cys Asp Ile Glu Gly Lys Asp Gly Lys Gln Tyr
1               5                   10                  15

Glu Ser Val Leu Met Val Ser Ile Asp Gln Leu Leu Asp Ser Met Lys
            20                  25                  30

Glu Ile Gly Ser Asn Cys Leu Asn Asn Glu Phe Asn Phe Phe Lys Arg
        35                  40                  45

His Ile Cys Asp Ala Asn Lys Glu Gly Met Phe Leu Phe Arg Ala Ala
    50                  55                  60
```

```
Arg Lys Leu Arg Gln Phe Leu Lys Met Asn Ser Thr Gly Asp Phe Asp
 65                  70                  75                  80

Leu His Leu Leu Lys Val Ser Glu Gly Thr Thr Ile Leu Leu Asn Cys
                 85                  90                  95

Thr Gly Gln Val Lys Gly Arg Lys Pro Ala Ala Leu Gly Glu Ala Gln
            100                 105                 110

Pro Thr Lys Ser Leu Glu Glu Asn Lys Ser Leu Lys Glu Gln Lys Lys
        115                 120                 125

Leu Asn Asp Leu Cys Phe Leu Lys Arg Leu Leu Gln Glu Ile Lys Thr
130                 135                 140

Cys Trp Asn Lys Ile Leu Met Gly Thr Lys Glu His Arg Asn Thr Gly
145                 150                 155                 160

Arg Gly Gly Glu Glu Lys Lys Lys Glu Lys Glu Lys Glu Glu Gln Glu
                165                 170                 175

Glu Arg Glu Thr Lys Thr Pro Glu Cys Pro Ser His Thr Gln Pro Leu
            180                 185                 190

Gly Val Phe Leu Phe Pro Pro Lys Pro Lys Asp Thr Leu Met Ile Ser
        195                 200                 205

Arg Thr Pro Glu Val Thr Cys Val Val Val Asp Val Ser Gln Glu Asp
210                 215                 220

Pro Glu Val Gln Phe Asn Trp Tyr Val Asp Gly Val Glu Val His Asn
225                 230                 235                 240

Ala Lys Thr Lys Pro Arg Glu Glu Gln Phe Asn Ser Thr Tyr Arg Val
                245                 250                 255

Val Ser Val Leu Thr Val Leu His Gln Asp Trp Leu Asn Gly Lys Glu
            260                 265                 270

Tyr Lys Cys Lys Val Ser Asn Lys Gly Leu Pro Ser Ser Ile Glu Lys
        275                 280                 285

Thr Ile Ser Lys Ala Lys Gly Gln Pro Arg Glu Pro Gln Val Tyr Thr
290                 295                 300

Leu Pro Pro Ser Gln Glu Glu Met Thr Lys Asn Gln Val Ser Leu Thr
305                 310                 315                 320

Cys Leu Val Lys Gly Phe Tyr Pro Ser Asp Ile Ala Val Glu Trp Glu
                325                 330                 335

Ser Asn Gly Gln Pro Glu Asn Asn Tyr Lys Thr Thr Pro Pro Val Leu
            340                 345                 350

Asp Ser Asp Gly Ser Phe Phe Leu Tyr Ser Arg Leu Thr Val Asp Lys
        355                 360                 365

Ser Arg Trp Gln Glu Gly Asn Val Phe Ser Cys Ser Val Met His Glu
370                 375                 380

Ala Leu His Asn His Tyr Thr Gln Lys Ser Leu Ser Leu Ser Leu Gly
385                 390                 395                 400

Lys

<210> SEQ ID NO 26
<211> LENGTH: 397
<212> TYPE: PRT
<213> ORGANISM: Artificial Sequence
<220> FEATURE:
<223> OTHER INFORMATION: amino acid sequence of human IL-7 fused hyFc

<400> SEQUENCE: 26

Asp Cys Asp Ile Glu Gly Lys Asp Gly Lys Gln Tyr Glu Ser Val Leu
1               5                   10                  15
```

```
Met Val Ser Ile Asp Gln Leu Leu Asp Ser Met Lys Glu Ile Gly Ser
             20                  25                  30

Asn Cys Leu Asn Asn Glu Phe Asn Phe Phe Lys Arg His Ile Cys Asp
         35                  40                  45

Ala Asn Lys Glu Gly Met Phe Leu Phe Arg Ala Ala Arg Lys Leu Arg
     50                  55                  60

Gln Phe Leu Lys Met Asn Ser Thr Gly Asp Phe Asp Leu His Leu Leu
 65                  70                  75                  80

Lys Val Ser Glu Gly Thr Thr Ile Leu Leu Asn Cys Thr Gly Gln Val
             85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
            115                 120                 125

Cys Phe Leu Lys Arg Leu Leu Gln Glu Ile Lys Thr Cys Trp Asn Lys
    130                 135                 140

Ile Leu Met Gly Thr Lys Glu His Arg Asn Thr Gly Arg Gly Gly Glu
145                 150                 155                 160

Glu Lys Lys Lys Glu Lys Glu Lys Glu Gln Glu Glu Arg Glu Thr
                165                 170                 175

Lys Thr Pro Glu Cys Pro Ser His Thr Gln Pro Leu Gly Val Phe Leu
                180                 185                 190

Phe Pro Pro Lys Pro Lys Asp Thr Leu Met Ile Ser Arg Thr Pro Glu
    195                 200                 205

Val Thr Cys Val Val Val Asp Val Ser Gln Glu Asp Pro Glu Val Gln
210                 215                 220

Phe Asn Trp Tyr Val Asp Gly Val Glu Val His Asn Ala Lys Thr Lys
225                 230                 235                 240

Pro Arg Glu Glu Gln Phe Asn Ser Thr Tyr Arg Val Val Ser Val Leu
                245                 250                 255

Thr Val Leu His Gln Asp Trp Leu Asn Gly Lys Glu Tyr Lys Cys Lys
            260                 265                 270

Val Ser Asn Lys Gly Leu Pro Ser Ser Ile Glu Lys Thr Ile Ser Lys
            275                 280                 285

Ala Lys Gly Gln Pro Arg Glu Pro Gln Val Tyr Thr Leu Pro Pro Ser
    290                 295                 300

Gln Glu Glu Met Thr Lys Asn Gln Val Ser Leu Thr Cys Leu Val Lys
305                 310                 315                 320

Gly Phe Tyr Pro Ser Asp Ile Ala Val Glu Trp Glu Ser Asn Gly Gln
                325                 330                 335

Pro Glu Asn Asn Tyr Lys Thr Thr Pro Pro Val Leu Asp Ser Asp Gly
            340                 345                 350

Ser Phe Phe Leu Tyr Ser Arg Leu Thr Val Asp Lys Ser Arg Trp Gln
    355                 360                 365

Glu Gly Asn Val Phe Ser Cys Ser Val Met His Glu Ala Leu His Asn
370                 375                 380

His Tyr Thr Gln Lys Ser Leu Ser Leu Ser Leu Gly Lys
385                 390                 395
```

<210> SEQ ID NO 27
<211> LENGTH: 395
<212> TYPE: PRT
<213> ORGANISM: Artificial Sequence
<220> FEATURE:
<223> OTHER INFORMATION: amino acid sequence of human IL-7 fused nonlytic mouse Fc

<400> SEQUENCE: 27

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His Ala Ser Ala Glu Pro Arg Gly Pro
145                 150                 155                 160

Thr Ile Lys Pro Cys Pro Pro Cys Lys Cys Pro Ala Pro Asn Leu Glu
                165                 170                 175

Gly Gly Pro Ser Val Phe Ile Phe Pro Pro Lys Ile Lys Asp Val Leu
            180                 185                 190

Met Ile Ser Leu Ser Pro Ile Val Thr Cys Val Val Val Asp Val Ser
        195                 200                 205

Glu Asp Asp Pro Asp Val Gln Ile Ser Trp Phe Val Asn Asn Val Glu
    210                 215                 220

Val His Thr Ala Gln Thr Gln Thr His Arg Glu Asp Tyr Asn Ser Thr
225                 230                 235                 240

Leu Arg Val Val Ser Ala Leu Pro Ile Gln His Gln Asp Trp Met Ser
                245                 250                 255

Gly Lys Ala Phe Ala Cys Ala Val Asn Asn Lys Asp Leu Pro Ala Pro
            260                 265                 270

Ile Glu Arg Thr Ile Ser Lys Pro Lys Gly Ser Val Arg Ala Pro Gln
        275                 280                 285

Val Tyr Val Leu Pro Pro Glu Glu Glu Met Thr Lys Lys Gln Val
    290                 295                 300

Thr Leu Thr Cys Met Val Thr Asp Phe Met Pro Glu Asp Ile Tyr Val
305                 310                 315                 320

Glu Trp Thr Asn Asn Gly Lys Thr Glu Leu Asn Tyr Lys Asn Thr Glu
                325                 330                 335

Pro Val Leu Asp Ser Asp Gly Ser Tyr Phe Met Tyr Ser Lys Leu Arg
            340                 345                 350

Val Glu Lys Lys Asn Trp Val Glu Arg Asn Ser Tyr Ser Cys Ser Val
        355                 360                 365

Val His Glu Gly Leu His Asn His His Thr Thr Lys Ser Phe Ser Arg
    370                 375                 380

Thr Pro Gly Lys Gly Gly Gly Asn Ser Gly Ser
385                 390                 395

<210> SEQ ID NO 28
<211> LENGTH: 531
<212> TYPE: DNA
<213> ORGANISM: Artificial Sequence
<220> FEATURE:
<223> OTHER INFORMATION: nucleotide sequence of human IL-7

<400> SEQUENCE: 28

```
atgttccacg tgagcttcag gtacatcttc ggcctgccac ccctgatcct ggtgctgctg      60
cctgtggcca gctccgactg cgacatcgag ggaaaagacg gcaagcagta cgaaagcgtg     120
ctgatggtgt ccatcgacca gctgctggat tctatgaagg agattgggag taactgcctg     180
aacaatgagt tcaacttctt caaacggcac atttgtgatg ccaacaagga gggaatgttc     240
ctgtttcggg ccgctagaaa actgaggcag ttcctgaaga tgaacagcac cggagacttt     300
gatctgcatc tgctgaaagt gtctgagggc accacaatcc tgctgaactg cactgggcag     360
gtgaaaggaa ggaagcctgc cgctctggga gaggctcagc caaccaagtc actggaggaa     420
aacaaaagcc tgaaggaaca agagaaactg aatgacctgt gctttctgaa acggctgctg     480
caggagatca aacatgttg gaacaagatt ctgatgggca caaggaaca c                531
```

<210> SEQ ID NO 29
<211> LENGTH: 534
<212> TYPE: DNA
<213> ORGANISM: Artificial Sequence
<220> FEATURE:
<223> OTHER INFORMATION: nucleotide sequence of modified IL-7(M)

<400> SEQUENCE: 29

```
atgttccacg tgagcttcag atacatcttc ggcctgcccc ccctgatcct ggtgctgctg      60
cccgtggcca gcagcatgga ctgcgacatc gagggcaagg acggcaagca gtacgagagc     120
gtgctgatgg tgagcatcga ccagctgctg gacagcatga aggagatcgg cagcaactgc     180
ctgaacaacg agttcaactt cttcaagaga cacatctgcg acgccaacaa ggagggcatg     240
ttcctgttca gagccgccag aaagctgaga cagttcctga gatgaacag caccggcgac     300 ttcgacctgc acctgctgaa ggtgagcgag ggcacaacca tcctgctgaa ctgcaccggc     360
caggtgaagg gcagaaagcc cgccgccctg ggcgaggccc agcccaccaa gagcctggag     420
gagaacaaga gcctgaagga gcagaagaag ctgaacgacc tgtgcttcct gaagagactg     480
ctgcaggaga tcaagaccct gctggaacaag atcctgatgg gcaccaagga gcac            534
```

<210> SEQ ID NO 30
<211> LENGTH: 537
<212> TYPE: DNA
<213> ORGANISM: Artificial Sequence
<220> FEATURE:
<223> OTHER INFORMATION: nucleotide sequence of modified IL-7(MM)

<400> SEQUENCE: 30

```
atgttccacg tgagcttcag atacatcttc ggcctgcccc ccctgatcct ggtgctgctg      60
cccgtggcca gcagcatgat ggactgcgac atcgagggca aggacggcaa gcagtacgag     120
agcgtgctga tggtgagcat cgaccagctg ctggacagca tgaaggagat cggcagcaac     180
tgcctgaaca acgagttcaa cttcttcaag agacacatct gcgacgccaa caaggagggc     240
atgttcctgt tcagagccgc cagaaagctg agacagttcc tgaagatgaa cagcaccggc     300
gacttcgacc tgcacctgct gaaggtgagc gagggcacaa ccatcctgct gaactgcacc     360
ggccaggtga agggcagaaa gcccgccgcc ctgggcgagg cccagcccac caagagcctg     420
```

| gaggagaaca agagcctgaa ggagcagaag aagctgaacg acctgtgctt cctgaagaga | 480 |
| ctgctgcagg agatcaagac ctgctggaac aagatcctga tgggcaccaa ggagcac | 537 |

<210> SEQ ID NO 31
<211> LENGTH: 540
<212> TYPE: DNA
<213> ORGANISM: Artificial Sequence
<220> FEATURE:
<223> OTHER INFORMATION: nucleotide sequence of modified IL-7(MMM)

<400> SEQUENCE: 31

| atgttccacg tgagcttcag atacatcttc ggcctgcccc cctgatcct ggtgctgctg | 60 |
| cccgtggcca gcagcatgat gatggactgc gacatcgagg caaggacgg caagcagtac | 120 |
| gagagcgtgc tgatggtgag catcgaccag ctgctggaca gcatgaagga gatcggcagc | 180 |
| aactgcctga caacgagtt caacttcttc aagagacaca tctgcgacgc caacaaggag | 240 |
| ggcatgttcc tgttcagagc cgccagaaag ctgagacagt tcctgaagat gaacagcacc | 300 |
| ggcgacttcg acctgcacct gctgaaggtg agcgagggca caaccatcct gctgaactgc | 360 |
| accggccagg tgaagggcag aaagcccgcc gccctgggcg aggcccagcc caccaagagc | 420 |
| ctggaggaga caagagcct gaaggagcag aagaagctga cgacctgtg cttcctgaag | 480 |
| agactgctgc aggagatcaa gacctgctgg aacaagatcc tgatgggcac caaggagcac | 540 |

<210> SEQ ID NO 32
<211> LENGTH: 540
<212> TYPE: DNA
<213> ORGANISM: Artificial Sequence
<220> FEATURE:
<223> OTHER INFORMATION: nucleotide sequence of modified IL-7(MGM)

<400> SEQUENCE: 32

| atgttccacg tgagcttcag gtacatcttc ggcctgccac cctgatcct ggtgctgctg | 60 |
| cctgtggcca gctccatggg gatggactgc gacatcgagg gaaaagacgg caagcagtac | 120 |
| gaaagcgtgc tgatggtgtc catcgaccag ctgctggatt ctatgaagga gattgggagt | 180 |
| aactgcctga caatgagtt caacttcttc aaacggcaca tttgtgatgc caacaaggag | 240 |
| ggaatgttcc tgtttcgggc cgctagaaaa ctgaggcagt tcctgaagat gaacagcacc | 300 |
| ggagactttg atctgcatct gctgaaagtg tctgagggca ccacaatcct gctgaactgc | 360 |
| actgggcagg tgaaaggaag gaagcctgcc gctctgggag aggctcagcc aaccaagtca | 420 |
| ctggaggaaa acaaaagcct gaaggaacag aagaaactga tgacctgtg ctttctgaaa | 480 |
| cggctgctgc aggagatcaa aacatgttgg aacaagattc tgatgggcac caaggagcac | 540 |

<210> SEQ ID NO 33
<211> LENGTH: 540
<212> TYPE: DNA
<213> ORGANISM: Artificial Sequence
<220> FEATURE:
<223> OTHER INFORMATION: nucleotide sequence of modified IL-7(DDD)

<400> SEQUENCE: 33

| atgttccacg tgagcttcag atacatcttc ggcctgcccc cctgatcct ggtgctgctg | 60 |
| cccgtggcca gcgcgacga tgacgactgc gacatcgagg caaggacgg caagcagtac | 120 |
| gagagcgtgc tgatggtgag catcgaccag ctgctggaca gcatgaagga gatcggcagc | 180 |
| aactgcctga caacgagtt caacttcttc aagagacaca tctgcgacgc caacaaggag | 240 |

```
ggcatgttcc tgttcagagc cgccagaaag ctgagacagt tcctgaagat gaacagcacc    300
ggcgacttcg acctgcacct gctgaaggtg agcgagggca caaccatcct gctgaactgc    360
accggccagg tgaagggcag aaagcccgcc gccctgggcg aggcccagcc caccaagagc    420
ctggaggaga caagagcct gaaggagcag aagaagctga cgacctgtg cttcctgaag     480 agactgctgc aggagatcaa gacctgctgg aacaagatcc tgatgggcac caaggagcac    540
```

<210> SEQ ID NO 34
<211> LENGTH: 543
<212> TYPE: DNA
<213> ORGANISM: Artificial Sequence
<220> FEATURE:
<223> OTHER INFORMATION: nucleotide sequence of modified IL-7(MMMM)

<400> SEQUENCE: 34

```
atgttccacg tgagcttcag atacatcttc ggcctgcccc ccctgatcct ggtgctgctg     60
cccgtggcca gcagcatgat gatgatggac tgcgacatcg agggcaagga cggcaagcag    120
tacgagagcg tgctgatggt gagcatcgac cagctgctgg acagcatgaa ggagatcggc    180
agcaactgcc tgaacaacga gttcaacttc ttcaagagac acatctgcga cgccaacaag    240
gagggcatgt tcctgttcag agccgccaga aagctgagac agttcctgaa gatgaacagc    300
accggcgact tcgacctgca cctgctgaag gtgagcgagg gcacaaccat cctgctgaac    360
tgcaccggcc aggtgaaggg cagaaagccc gccgccctgg gcgaggccca gcccaccaag    420
agcctggagg agaacaagag cctgaaggag cagaagaagc tgaacgacct gtgcttcctg    480
aagagactgc tgcaggagat caagacctgc tggaacaaga tcctgatggg caccaaggag    540
cac                                                                   543
```

<210> SEQ ID NO 35
<211> LENGTH: 1284
<212> TYPE: DNA
<213> ORGANISM: Artificial Sequence
<220> FEATURE:
<223> OTHER INFORMATION: nucleotide sequence of modified IL-7(M) fused
    hyFc

<400> SEQUENCE: 35

```
atgttccacg tgagcttcag atacatcttc ggcctgcccc ccctgatcct ggtgctgctg     60
cccgtggcca gcagcatgga ctgcgacatc gagggcaagg acggcaagca gtacgagagc    120
gtgctgatgg tgagcatcga ccagctgctg gacagcatga aggagatcgg cagcaactgc    180
ctgaacaacg agttcaactt cttcaagaga cacatctgcg acgccaacaa ggagggcatg    240
ttcctgttca gagccgccag aaagctgaga cagttcctga gatgaacag caccggcgac    300 ttcgacctgc acctgctgaa ggtgagcgag gcacaacca tcctgctgaa ctgcaccggc    360
caggtgaagg gcagaaagcc cgccgccctg ggcgaggccc agcccaccaa gagcctggag    420
gagaacaaga gcctgaagga gcagaagaag ctgaacgacc tgtgcttcct gaagagactg    480
ctgcaggaga tcaagacctg ctggaacaag atcctgatgg gcaccaagga gcacaggaac    540
acaggcagag gcggcgagga agaagaagaag gagaaggaga aggaggagca ggaggaaaga    600
gagaccaaga ccccccgagtg ccccagccac acccagcccc tgggcgtgtt cctgttccct    660
cccaagccca aggacaccct gatgatcagc agaacccccg aggtgacctg cgtggtcgtg    720
gatgtgagcc aggaagatcc cgaagtgcag ttcaactggt acgtggatgg cgtggaagtg    780
cacaacgcca agaccaagcc cagagaagag cagttcaact ccacctacag agtggtgagc    840
```

```
gtgctgaccg tgctgcacca ggactggctg aacggcaagg agtacaagtg caaggtgtcc      900
aacaaaggcc tgcccagctc catcgagaag accatcagca agccaaagg ccagcccaga       960 gaaccccagg tgtacaccct gcctcccagc aggaagaga tgaccaagaa ccaggtgtcc      1020
ctgacctgcc tggtgaaagg cttctacccc agcgacatcg ccgtggagtg ggaaagcaac     1080
ggccagcccg agaacaatta caagacaacc cctcccgtgc tggatagcga tggcagcttc     1140
tttctgtaca gcagactgac cgtggacaag agcagatggc aggaaggcaa cgtgttcagc     1200
tgcagcgtga tgcacgaagc cctgcacaac cactacaccc agaagagcct gtccctgagc     1260
ctgggcaagt gactcgagtc taga                                            1284
```

<210> SEQ ID NO 36
<211> LENGTH: 1272
<212> TYPE: DNA
<213> ORGANISM: Artificial Sequence
<220> FEATURE:
<223> OTHER INFORMATION: nucleotide sequence of modified IL-7(MM) fused
      hyFc

<400> SEQUENCE: 36

```
atgttccacg tgagcttcag atacatcttc ggcctgcccc ccctgatcct ggtgctgctg       60
cccgtggcca gcagcatgat ggactgcgac atcgagggca aggacggcaa gcagtacgag      120
agcgtgctga tggtgagcat cgaccagctg ctggacagca tgaaggagat cggcagcaac     180
tgcctgaaca acgagttcaa cttcttcaag agacacatct gcgacgccaa caaggagggc     240
atgttcctgt tcagagccgc cagaaagctg agacagttcc tgaagatgaa cagcaccggc     300
gacttcgacc tgcacctgct gaaggtgagc gagggcacaa ccatcctgct gaactgcacc     360
ggccaggtga agggcagaaa gcccgccgcc ctgggcgagg cccagcccac caagagcctg     420
gaggagaaca gagcctgaa ggagcagaag aagctgaacg acctgtgctt cctgaagaga     480
ctgctgcagg agatcaagac ctgctggaac aagatcctga tgggcaccaa ggagcacagg     540
aacacaggca gaggcggcga ggagaagaag aaggagaagg agaaggagga gcaggaggaa     600
agagagacca gacccccga gtgccccagc cacacccagc ccctgggcgt gttcctgttc     660
cctcccaagc ccaaggacac cctgatgatc agcagaaccc ccgaggtgac ctgcgtggtc     720
gtggatgtga gccaggaaga tcccgaagtg cagttcaact ggtacgtgga tggcgtggaa     780
gtgcacaacg ccaagaccaa gcccagagaa gagcagttca ctccaccta cagagtggtg     840 agcgtgctga ccgtgctgca ccaggactgg ctgaacggca aggagtacaa gtgcaaggtg     900
tccaacaaag gcctgcccag ctccatcgag aagaccatca gcaaagccaa ggccagccc     960 agagaacccc aggtgtacac cctgcctccc agccaggaag atgaccaa gaaccaggtg     1020 tccctgacct gcctggtgaa aggcttctac cccagcgaca tcgccgtgga gtgggaaagc     1080
aacggccagc ccgagaacaa ttacaagaca ccctcccg tgctggatag cgatggcagc     1140
ttctttctgt acagcagact gaccgtggac aagagcagat ggcaggaagg caacgtgttc     1200
agctgcagcg tgatgcacga agccctgcac aaccactaca cccagaagag cctgtccctg     1260
agcctgggca ag                                                         1272
```

<210> SEQ ID NO 37
<211> LENGTH: 1275
<212> TYPE: DNA
<213> ORGANISM: Artificial Sequence
<220> FEATURE:
<223> OTHER INFORMATION: nucleotide sequence of modified IL-7(MMM) fused
      hyFc

<400> SEQUENCE: 37

```
atgttccacg tgagcttcag atacatcttc ggcctgcccc cctgatcct ggtgctgctg    60
cccgtggcca gcagcatgat gatggactgc gacatcgagg gcaaggacgg caagcagtac   120
gagagcgtgc tgatggtgag catcgaccag ctgctggaca gcatgaagga gatcggcagc   180
aactgcctga acaacgagtt caacttcttc aagagacaca tctgcgacgc caacaaggag   240
ggcatgttcc tgttcagagc cgccagaaag ctgagacagt tcctgaagat gaacagcacc   300
ggcgacttcg acctgcacct gctgaaggtg agcgagggca accatcctg ctgaactgc    360
accggccagt gaagggcag aaagcccgcc gccctgggcg aggcccagcc caccaagagc   420
ctggaggaga caagagcct gaaggagcag aagaagctga cgacctgtg cttcctgaag   480
agactgctgc aggagatcaa gacctgctgg aacaagatcc tgatgggcac caaggagcac   540
aggaacacag gcagaggcgg cgaggagaag aagaaggaga aggagaagga ggagcaggag   600
gaaagagaga ccaagacccc cgagtgcccc agccacaccc agcccctggg cgtgttcctg   660
ttccctccca gcccaaggac accctgatg atcagcagaa ccccgaggt gacctgcgtg    720
gtcgtggatg tgagccagga agatcccgaa gtgcagttca actggtacgt ggatggcgtg    780
gaagtgcaca cgccaagac caagcccaga gaagagcagt tcaactccac ctacagagtg    840
gtgagcgtgc tgaccgtgct gcaccaggac tggctgaacg gcaaggagta caagtgcaag    900
gtgtccaaca aggcctgcc cagctccatc gagaagacca tcagcaaagc caaggccag    960
cccagagaac cccaggtgta caccctgcct cccagccagg aagagatgac caagaaccag   1020
gtgtccctga cctgcctggt gaaaggcttc taccccagcg acatcgccgt ggagtgggaa   1080
agcaacggcc agcccgagaa caattacaag acaacccctc ccgtgctgga tagcgatggc   1140
agcttctttc tgtacagcag actgaccgtg gacaagagca tgcagga aggcaacgtg   1200
ttcagctgca gcgtgatgca cgaagccctg cacaaccact acacccagaa gagcctgtcc   1260
ctgagcctgg gcaag                                                   1275
```

<210> SEQ ID NO 38
<211> LENGTH: 1275
<212> TYPE: DNA
<213> ORGANISM: Artificial Sequence
<220> FEATURE:
<223> OTHER INFORMATION: nucleotide sequence of modified IL-7(MGM) fused hyFc

<400> SEQUENCE: 38

```
atgttccacg tgagcttcag gtacatcttc ggcctgccac cctgatcct ggtgctgctg    60
cctgtggcca gctccatggg gatggactgc gacatcgagg gaaaagacgg caagcagtac   120
gaaagcgtgc tgatggtgtc catcgaccag ctgctggatt ctatgaagga gattgggagt   180
aactgcctga acaatgagtt caacttcttc aaacggcaca tttgtgatgc caacaaggag   240
ggaatgttcc tgtttcgggc cgctagaaaa ctgaggcagt tcctgaagat gaacagcacc   300
ggagactttg atctgcatct gctgaaagtg tctgagggca ccacaatcct gctgaactgc   360
actgggcagt gaaaggaag gaagcctgcc gctctgggag aggctcagcc aaccaagtca   420
ctggaggaaa caaaagcct gaaggaacag aagaaactga atgacctgtg cttctgaaa   480
cggctgctgc aggagatcaa acatgttgaa caagattc tgatgggcac aaaggaacac   540
cgcaatactg ggcggggcgg ggaggaaaag aaaaaggaga aggaaaagga ggaacaggag   600
gaaagagaga ctaagacccc agaatgtccc agccatactc agccctggg ggtgttcctg   660
```

```
tttcccccta aacctaagga taccctgatg atcagcagga cacccgaggt gacctgcgtg      720
gtcgtggatg tgagccagga agatcccgaa gtgcagttca actggtacgt ggatggcgtg      780
gaagtgcaca acgccaagac caagcccaga gaagagcagt tcaactccac ctacagagtg      840
gtgagcgtgc tgaccgtgct gcaccaggac tggctgaacg gcaaggagta caagtgcaag      900
gtgtccaaca aaggcctgcc cagctccatc gagaagacca tcagcaaagc caaggccag      960 cccagagaac cccaggtgta caccctgcct cccagccagg aagagatgac caagaaccag     1020
gtgtccctga cctgcctggt gaaaggcttc taccccagcg acatcgccgt ggagtgggaa     1080
agcaacggcc agcccgagaa caattacaag acaacccctc ccgtgctgga tagcgatggc     1140
agcttctttc tgtacagcag actgaccgtg gacaagagca tggcagga aggcaacgtg      1200 ttcagctgca gcgtgatgca cgaagccctg cacaaccact acacccagaa gagcctgtcc     1260
ctgagcctgg gcaag                                                      1275

<210> SEQ ID NO 39
<211> LENGTH: 1278
<212> TYPE: DNA
<213> ORGANISM: Artificial Sequence
<220> FEATURE:
<223> OTHER INFORMATION: nucleotide sequence of modified IL-7(MMMM)
      fused hyFc

<400> SEQUENCE: 39
atgttccacg tgagcttcag atacatcttc ggcctgcccc ccctgatcct ggtgctgctg       60
cccgtggcca gcagcatgat gatgatggac tgcgacatcg agggcaagga cggcaagcag      120
tacgagagcg tgctgatggt gagcatcgac cagctgctgg acagcatgaa ggagatcggc      180
agcaactgcc tgaacaacga gttcaacttc ttcaagagac acatctgcga cgccaacaag      240
gagggcatgt tcctgttcag agccgccaga aagctgagac agttcctgaa gatgaacagc      300
accgccgact cgacctgca cctgctgaag gtgagcgagg gcacaaccat cctgctgaac      360
tgcaccggcc aggtgaaggg cagaaagccc gccgccctgg gcgaggccca gcccaccaag      420
agcctggaga gaacaagag cctgaaggag cagaagaagc tgaacgacct gtgcttcctg      480
aagagactgc tgcaggagat caagacctgc tggaacaaga tcctgatggg caccaaggag      540
cacaggaaca caggcagagg cggcgaggag aagaagaagg agaaggagaa ggaggagcag      600
gaggaaagag agaccaagac ccccgagtgc ccagccaca cccagccct gggcgtgttc      660 ctgttcccct ccaagcccaa ggacaccctg atgatcagca gaaccccga ggtgacctgc      720 gtggtcgtgg atgtgagcca ggaagatccc gaagtgcagt tcaactggta cgtggatggc      780
gtggaagtgc acaacgccaa gaccaagccc agagaagagc agttcaactc cacctacaga      840
gtggtgagcg tgctgaccgt gctgcaccag gactggctga acggcaagga gtacaagtgc      900
aaggtgtcca acaaaggcct gcccagctcc atcgagaaga ccatcagcaa agccaaggc      960 cagcccagag aacccaggt gtacaccctg cctcccagcc aggaagagat gaccaagaac     1020
caggtgtccc tgacctgcct ggtgaaaggc ttctacccca gcgacatcgc cgtggagtgg     1080
gaaagcaacg ccagcccga acaattacaa gacaacccc tcccgtgct ggatagcgat     1140 ggcagcttct ttctgtacag cagactgacc gtggacaaga gcagatggca ggaaggcaac     1200
gtgttcagct gcagcgtgat gcacgaagcc ctgcacaacc actacaccca gaagagcctg     1260
tccctgagcc tgggcaag                                                   1278
```

```
<210> SEQ ID NO 40
<211> LENGTH: 4
<212> TYPE: PRT
<213> ORGANISM: Artificial Sequence
<220> FEATURE:
<223> OTHER INFORMATION: Synthetic oligopeptide

<400> SEQUENCE: 40

Met Met Met Met
1
```